United States Patent
Kanegae et al.

(10) Patent No.: US 11,089,993 B2
(45) Date of Patent: Aug. 17, 2021

(54) DEVICE AND METHOD FOR MEASURING SLEEP STATE, PHASE COHERENCE CALCULATION DEVICE, BODY VIBRATION SIGNAL MEASUREMENT DEVICE, STRESS LEVEL MEASUREMENT DEVICE, SLEEP STATE MEASUREMENT DEVICE, AND CARDIAC WAVEFORM EXTRACTION METHOD

(71) Applicant: Health Sensing Co., Ltd., Hachioji (JP)

(72) Inventors: Masatomo Kanegae, Hachioji (JP); Tsutomu Fujita, Mobara (JP); Kyuichi Niizeki, Yonezawa (JP)

(73) Assignee: Health Sensing Co., Ltd., Hachioji (JP)

( * ) Notice: Subject to any disclaimer, the term of this patent is extended or adjusted under 35 U.S.C. 154(b) by 190 days.

(21) Appl. No.: 16/077,350

(22) PCT Filed: Feb. 15, 2017

(86) PCT No.: PCT/JP2017/005556
§ 371 (c)(1),
(2) Date: Aug. 10, 2018

(87) PCT Pub. No.: WO2017/141976
PCT Pub. Date: Aug. 24, 2017

(65) Prior Publication Data
US 2019/0076084 A1    Mar. 14, 2019

(30) Foreign Application Priority Data

Feb. 15, 2016  (JP) .............................. JP2016-026008

(51) Int. Cl.
*A61B 5/00* (2006.01)
*A61B 5/024* (2006.01)
(Continued)

(52) U.S. Cl.
CPC .......... *A61B 5/4812* (2013.01); *A61B 5/0245* (2013.01); *A61B 5/02405* (2013.01); *A61B 5/08* (2013.01); *A61B 5/16* (2013.01)

(58) Field of Classification Search
CPC ..... A61B 5/02405; A61B 5/0245; A61B 5/08; A61B 5/16; A61B 5/4812
See application file for complete search history.

(56) References Cited

U.S. PATENT DOCUMENTS 5,411,029 A    5/1995  Hirai
6,415,174 B1 *  7/2002  Bebehani ............. A61B 5/0452
                                                    600/512

(Continued)

FOREIGN PATENT DOCUMENTS

CN    104545883    4/2015
JP    06-261865    9/1994

(Continued)

OTHER PUBLICATIONS

Niizeki et al., "Incoherent oscillations of respiratory sinus arrhythmia during acute mental stress in humans", first published Oct. 28, 2011, Am J Physiol Heart Circ Physiol 302: H359-H367 (Year: 2012).*

(Continued)

*Primary Examiner* — Jonathan T Kuo
*Assistant Examiner* — Vynn V Huh
(74) *Attorney, Agent, or Firm* — William C. Schrot; Jeffrey I. Auerbach; AuerbachSchrot LLC

(57) ABSTRACT

[Problem] To provide means by which sleep states can be measured, observed, or evaluated easily. [Solution] A sleep state measurement device that includes a phase coherence calculating means for calculating phase coherence on the basis of the instantaneous phase difference between the instantaneous phase of heart rate variability acquired from a (Continued)

sleeping animal and the instantaneous phase of the breathing pattern of the animal for the same time series as the heart rate variability.

17 Claims, 26 Drawing Sheets

(51) Int. Cl.
  *A61B 5/0245* (2006.01)
  *A61B 5/08* (2006.01)
  *A61B 5/16* (2006.01)
  *A61B 5/11* (2006.01)
  *A61B 5/318* (2021.01)

(56) References Cited

U.S. PATENT DOCUMENTS

| | | | |
|---|---|---|---|
| 2010/0249628 A1* | 9/2010 | Kortelainen | A61B 5/1102 600/527 |
| 2011/0034811 A1 | 2/2011 | Naujokat et al. | |
| 2011/0046434 A1* | 2/2011 | Schmeink | A61B 5/0816 600/27 |
| 2013/0310700 A1 | 11/2013 | Wiard et al. | |

FOREIGN PATENT DOCUMENTS

| | | |
|---|---|---|
| JP | 2011-517982 | 6/2011 |
| JP | 2011-521674 | 7/2011 |
| JP | 2013-099528 | 5/2013 |
| JP | 2013-202216 | 10/2013 |
| JP | 2014-507213 | 3/2014 |
| JP | 2017-064338 | 4/2017 |

OTHER PUBLICATIONS

Press Release of Faculty of Engineering, Yamagata University, Feb. 17, 2015.
International Search Report PCT/JP2017/005556 (WO 2017/141976) (dated 2017) (4 pages).
Written Opinion of the International Searching Authority PCT/JP2017/005556 (WO 2017/141976) (dated 2017) (Translation).
Niizeki, K., et al. (2012) "*Incoherent Oscillations of Respiratory Sinus Arrhythmia During Acute Mental Stress in Humans*," Am. J. Physiol. Heart Circ. Physiol. 302: H359-H367.
Chinese Office Action CN 201780008956.8 (dated Jul. 21, 2020) (11 pages); resubmitted along with an English translation thereof.

* cited by examiner

FIG. 4
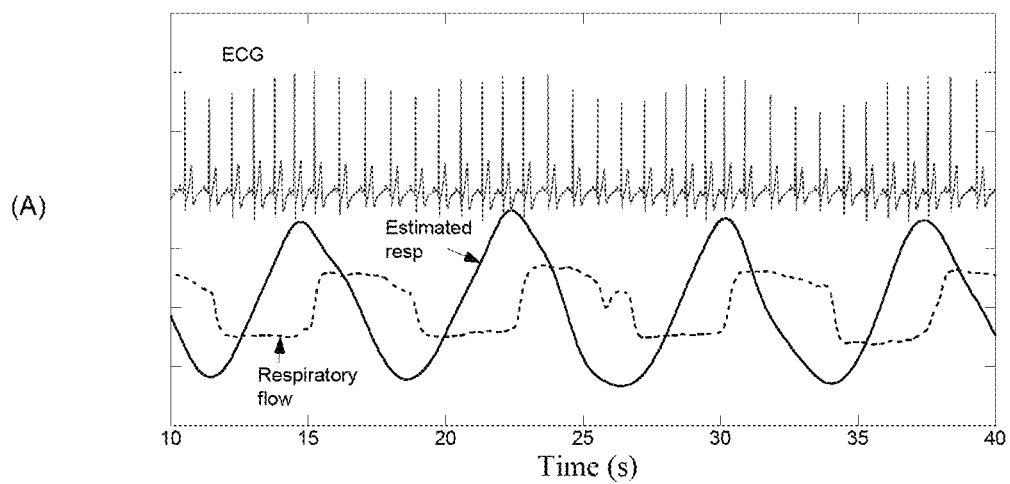
(A)
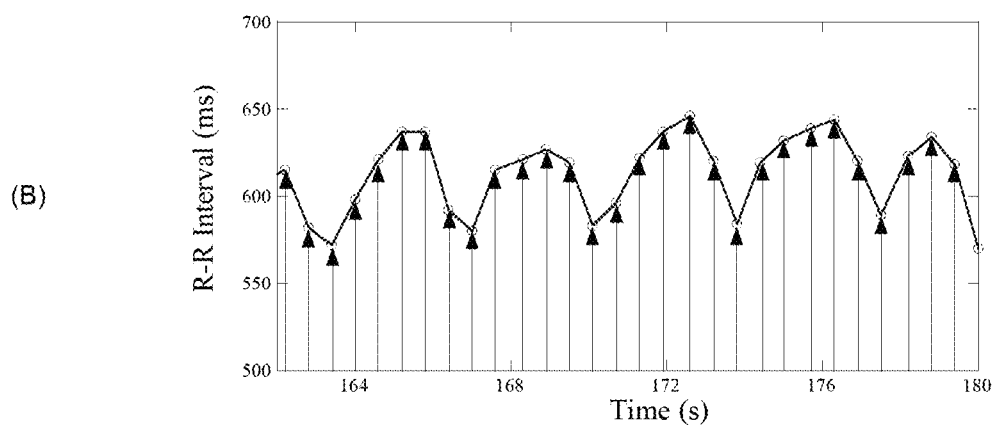
(B)
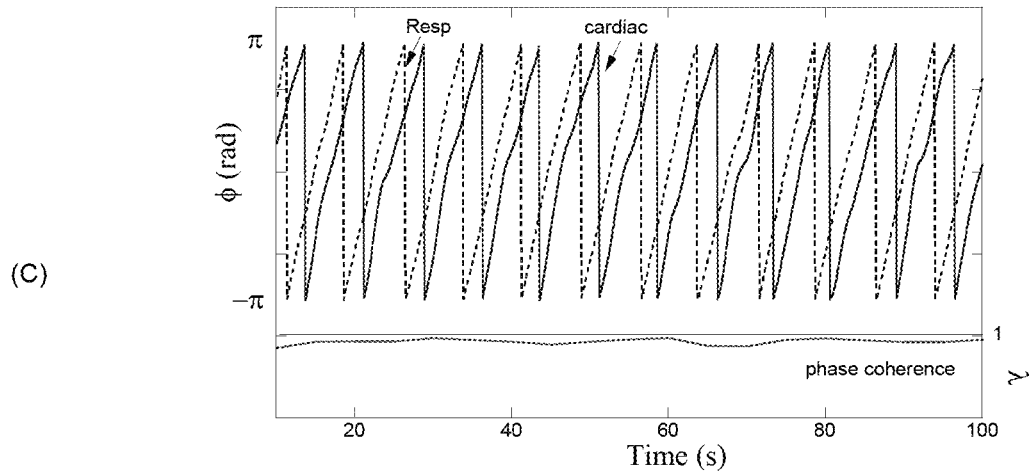
(C)

| Breathing Frequency (Hz) | 0.133 | 0.167 | 0.2 | 0.25 | 0.3 | 0.33 | 0.4 |
|---|---|---|---|---|---|---|---|
| Estimated Accuracy | 1.05±0.13 | 0.95±0.05 | 0.95±0.04 | 0.94±0.04 | 0.92±0.03 | 0.91±0.04 | 0.87±0.04 |

FIG. 8
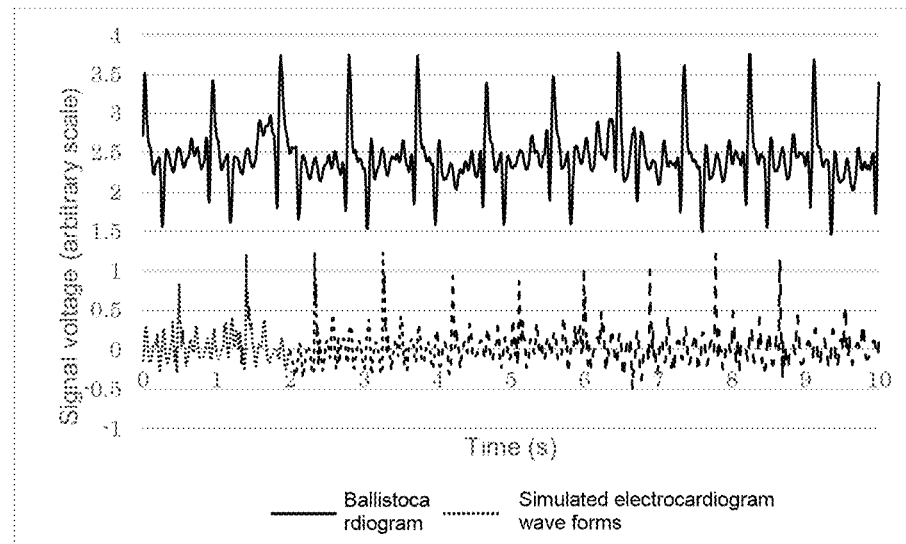
(A)
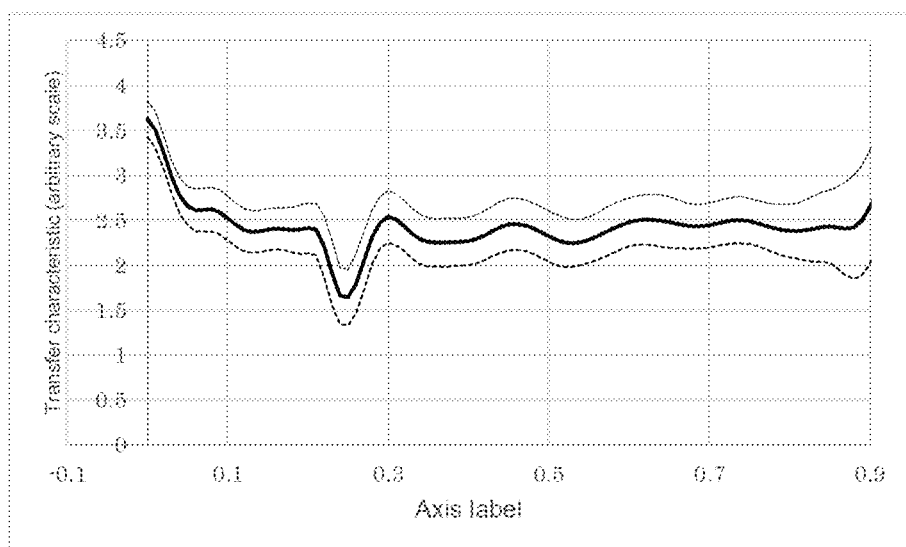
(B)

DEVICE AND METHOD FOR MEASURING SLEEP STATE, PHASE COHERENCE CALCULATION DEVICE, BODY VIBRATION SIGNAL MEASUREMENT DEVICE, STRESS LEVEL MEASUREMENT DEVICE, SLEEP STATE MEASUREMENT DEVICE, AND CARDIAC WAVEFORM EXTRACTION METHOD

FIELD OF THE INVENTION

This invention relates to a device or method that acquires information as an indicator of mental stress or sleep state based on biological information obtained from a subject, or related to a device or method that measures the sleep state of a subject. Furthermore, this invention related to a method that extracts heartbeat wave forms or breathing wave forms from biological information obtained from a subject. In addition, this invention relates to a bio-vibration signal measuring device that acquires bio-vibration signals containing both information about heartbeat and information about breathing from a subject using a vibration sensor as well as a device that measures stress state or sleep state based on phase coherence calculated from the acquired bio-vibration signals.

BACKGROUND OF THE INVENTION

As stress clue to social advancement is increasing, and the population ages with the birthrate on the decline, the patient population with breathing or cardiovascular diseases is on the rise. Examinations on breathing and cardiovascular functions and prophylaxis from such diseases become increasingly important. Conventionally, mental stress has been assessed by subjective assessment through diagnostic interview, measurement of physiological parameters such as blood pressure, heart rate, skin temperature, and perspiration, or measurement of humoral stress markers such as catecholamine and cortisol, which are mainly performed at medical institutions and cannot be performed by individuals.

For home medical care or preventive medicine, bio-signal measuring devices are proposed as devices that allow individuals to measure bio-signals such as blood oxygen saturation and pulse in daily life. Such proposed devices are especially designed to measure the bio-signals on blood vessels (arteries) of a finger to which a probe is readily attached. For example, Reference Patent 1 discloses a ring-type bio-signal measuring device which is attached to a finger. The concerned ring-type bio-signal measuring device is said to measure bio-signals such as pulse wave and blood oxygen saturation through blood vessels optically.

None-reference Patent 1 presents a method in which heartbeat fluctuations are extracted from measured electrocardiogram and then subjected to frequency analysis to estimate the autonomic activity as a stress indicator indirectly, but the indicator may be altered by breathing frequency or tidal volume, even in a stress-free state. The concerned method, therefore, does not serve as a generalized assessment method. There is an additional problem that substantial interindividual differences due to dependence on age and impact of physical fitness prevent the method from quantitative assessment.

None-reference Patent 2 discloses that phase coherence in instantaneous phase difference between fluctuations in heartbeat interval and breathing pattern is correlated with mental stress, indicating that the phase coherence may be used in assessment as a mental stress indicator. None-reference Patent 2 describes that electrocardiogram is obtained with electrodes attached to the chest; breathing pattern is measured with a breathing effort belt wrapped around the chest and abdomen; fluctuations in heartbeat interval (respiratory sinus arrhythmia) is calculated from the electrocardiogram; furthermore, instantaneous phase of the fluctuations in heartbeat interval is calculated; instantaneous phase of the breathing pattern is calculated; from the above data, instantaneous phase difference $\Psi(t)j$ between heartbeat and breathing rhythm at the time of t is obtained; and using the obtained instantaneous phase difference, phase coherence is calculated according to Equation (1). N in Equation (1) is the number of data samples, the mean of N data samples is determined.

[Equation 1]

$$\lambda(t_k) = \left| \frac{1}{N} \sum_{j=k-N/2}^{k+N/2} e^{i\Psi(t_j)} \right| \quad (1)$$

Phase coherence is a value between 0 and 1. As instantaneous phase difference between fluctuations in heartbeat interval and breathing pattern is reaching a constant relationship, the phase coherence value is becoming approximate to 1. As the instantaneous phase difference is reaching a random state, it is becoming approximate to 0. When a subject is relaxed at rest, the phase coherence is approximate to 1. When a subject is under mental stress, it is reduced. The phase coherence value therefore can be estimated using an indicator of normalized mental stress.

By the way, it is said that human sleep is largely divided into non-rapid eye movement (REM) sleep and REM sleep, which are alternated cyclically with a period of approximately 90 minutes. To assess quality and quantity of sleep (sleep cycle and sleep depth) objectively, polysomnographic recording is necessary. The measurement is performed at a medical institution or with the instrument rented from a medical institution, but multiple sensors for brain waves, electrocardiogram, electromyogram, and electrooculogram are necessary, accompanying complicated handling. In addition, multiple sensors have to be fixed to each site of the body, restricting movements of a subject. In addition, unconscious body movements during sleep may take the sensors off, resulting in failures of signal detection and state monitoring. Thus, such measurement has a problem. Furthermore, the device is large. Indicators used in the above measurement cannot be handled for assessment by an individual. Current measurement situations have not allowed individuals to assess the sleep quality. Therefore, a biometry method and corresponding device that allow individuals to monitor the stress state and sleep quality readily have been demanded.

In addition, if an elderly person dies alone or at a nursing home unfortunately; it is mostly difficult to identify either of accident and disease as the cause of death. To prevent such situation, a biological information measuring system that allows non-invasive and easy measurement without restriction to daily physical activities has been long awaited. Reference Patent 2 discloses detection of body vibration signals with non-restraint piezoelectric sensors which detect body vibrations of a subject and are placed on and under a bedpad or mattress. Furthermore, body vibration signals detected with piezoelectric sensors are amplified with a differential amplifier to extract body vibrations of a subject using a separation filter, including vibrations originated from heart beats (heart rate, 30-240/min; frequency range, 0.5-4 Hz), that from pulmonary breathing activity (breathing rate, ≤60/min; frequency range, ≤1 Hz), and snore vibrations from snore. In Reference Patent 2, presence of a subject at a specified place is judged when beating vibrations caused by heart beats, pulmonary breathing vibrations caused by pulmonary breathing activity, or snore vibrations are detected for the specified duration for the presence or longer; or absence of a subject at a specified place is judged when beating vibrations, pulmonary breathing vibrations, or snore vibrations not detected for the specified duration for the absence or longer.

The absence detection device in Reference Patent 2 acquires body vibration signals, using one piezoelectric sensor, and obtains 4 types of signals, including breathing, heartbeat, snore, and body movement by separating the body vibration signals with a frequency filter. It is disclosed that the frequency filter is comprised of either one or both of analog filters such as low-pass filter (LPF) and high-pass filter (HPF) consisting of condenser and resistance and operational amplifiers and digital filters in which body vibration signals are converted into digital signals with an A/D converter, and the resultant data in a numerical form are filtered by processing with a central processing unit (CPU).

LEADING TECHNICAL REFERENCE

Reference Patent

Reference Patent 1: PD 2006-325766 Official Gazette
Reference Patent 2: PD 2013-210367 Official Gazette None-Reference Patent None-reference Patent 1: Gary G Berntson, J. Thomas Bigger Jr. et al., "Heart rate variability: Origin, methods, and interpretive caveats". Psychophysiology (USA) Vol. 34, p. 623-648, 1997
None-reference Patent 2: Niizeki K. and Saitoh T., "Incoherent vibrations of respiratory sinus arrhythmia during acute mental stress in humans". American Journal of Physiology Heart and Circulatory Physiology (USA) Vol. 302, p. 359-367, 2012

SUMMARY OF THE INVENTION

Issues to be Resolved by the Invention

In recent years, sleep disorders have become more common, which may be related to stress, and thus a means that allows individuals to measure, monitor, or assess the sleep state readily as a part of self-care has been awaited. To assess quality and quantity of sleep (sleep cycle and sleep depth) objectively, however, measurement at a medical institution and large dedicated device are necessary, and the measurement in daily life activities is difficult. Furthermore, the conventional device requires multiple sensors to obtain brain waves, electrocardiogram, electromyogram, electrooculogram, and these sensors have to be fixed to each site of the body. In addition, because attachment of the sensors restricts movements, reduction of the number of sensors to the minimum possible has been requested. Because unconscious movements during sleep may take the sensors off, measurement with readily attachable sensors has been also desired. Furthermore, there has been a demand to alleviate the complicated handling associated with fixation of multiple sensors to each site of the body. Accordingly, a device that allows individuals to measure the stress state or sleep state readily has been desired.

The device that acquires information as a mental stress indicator is desired to be wearable and to have a configuration that would not disturb movements of the body wherever possible. From this aspect, the ring-type bio-signal measuring device as defined in Reference Patent 1 is desirable, because it can be attached to a finger. Such ring-type bio-signal measuring device, however, has a problem of large power consumption to operate a light-emitting diode (LED) part, because it measures absorbance of hemoglobin in blood as well as heartbeat based on fluctuations in absorbance synchronized with heartbeat, with an optical sensor that has an LED part. Furthermore, the bio-signal measuring device using the said optical sensor is required to irradiate blood vessels with light from the LED part. Therefore, there is a problem that displacement of light from a point above the blood vessel would result in a failure of the bio-signal measurement. The bio-signal measuring device has to be attached to an extremely limited site, and measures against displacement after the attachment have to be taken. Furthermore, the bio-signal measuring device as defined in Reference Patent 1 is claimed to be able to measure pulse based on pulse wave, but information about breathing cannot be measured.

As a separate issue, the stress assessment method as defined in None-reference Patent 1 has a problem of an inability to assess the stress quantitatively, because indicators may be altered even in a stress-free state as described above, and interindividual differences are substantial due to dependence on age and impact of physical fitness. The stress assessment method as defined in None-reference Patent 1 uses heartbeat rhythm fluctuations extracted from electrocardiogram as a stress indicator, but the concerned indicator is affected by heartbeat rhythm fluctuations, breathing frequency, and tidal volume, and thus may be altered even in a stress-free state. The method, therefore, does not serve as a generalized assessment method. There is an additional problem that substantial interindividual differences due to dependence on age and impact of physical fitness prevent the method from quantitative assessment.

The method as defined in None-reference Patent 2 is claimed to be able to assess stress based on phase coherence, which is obtained as follows: electrocardiogram is obtained with electrodes attached to the chest; breathing pattern is measured with a breathing effort belt wrapped around the chest and abdomen; and phase coherence is calculated from the heartbeat and breathing pattern. The method as defined in None-reference Patent 2, however, needs a sensor for electrocardiogram to detect heartbeat and another sensor to detect breathing pattern. Especially, the sensor to detect breathing pattern itself would cause stress through the attachment, if it measures breathing volume through a mask that covers the mouth and nose. In addition, such mask would prevent measurement during daily life activities, exercise, or sleep. Development of a method that readily allows stress assessment in a less-burdensome and stress-free state has been desired.

In addition, in a case where heartbeat information and breathing information are acquired from body vibration signals obtained with one piezoelectric sensor using a frequency filter as described in Reference Patent 2, the extracted breathing information and heartbeat information should be highly precise. Such acquisition of highly precise information has been desired as a challenge to be resolved. Especially, the following method has been desired: by this method, precise heartbeat information or breathing information that can be used in stress assessment as described above are acquired from signals containing multiple types of information, providing fluctuations in heartbeat interval and breathing pattern indirectly.

This invention is intended to resolve at least a part of the above subject.

Means to Resolve the Subject

To resolve the said subject, the sleep state measuring device in this invention includes a phase coherence calculation means that calculates phase coherence based on an instantaneous phase difference between instantaneous phase of fluctuations in heartbeat interval obtained during the subject's sleep and instantaneous phase in breathing pattern of the said subject in the same time series as that for fluctuations in heartbeat interval Furthermore, the sleep state measuring device may have an electrocardiogram measuring sensor and a breathing wave form extraction means that extracts signals related to breathing pattern from electrocardiogram of the subject measured with the said sensor. In addition, the sleep state measuring device may include a vibration measuring sensor, a heart rate interval calculation means that calculates fluctuations in heartbeat interval from signals measured with the said sensor, and a breathing wave form extraction means that extracts signals related to breathing pattern from signals measured with the said sensor. For the above sleep state measuring device, sampling frequency of the said sensor is desirably not less than 100 Hz. Furthermore, the said sensor is desirably a wearable sensor that can put on body of the subject, and the said wearable sensor is more desirably implemented on a wearing part that puts on a limb or head of the subject. Furthermore, the above sleep state measuring may have an assessment function that assesses the sleep state based on phase coherence calculated with the said phase coherence calculation means. The said assessment function, furthermore, may assess the breathing state during sleep based on the said breathing pattern.

The sleep state measuring method in this invention measures the sleep state based on phase coherence in instantaneous phase difference between fluctuations in heartbeat interval and breathing frequency in the same time series during sleep of the subject. Furthermore, the above sleep state measuring method may measure electrocardiogram of the said subject, and obtain signals related to breathing pattern from the measured electrocardiogram. The above sleep state measuring method may measure ballistocardiogram wave forms or bio-vibration signals of the said subject, and obtain signals related to fluctuations in heartbeat interval and breathing pattern from the measured ballistocardiogram wave forms or bio-vibration signals. Furthermore, in this method it is desirable to estimate transfer characteristic between ballistocardioaction from ballistocardiogram wave forms or bio-vibration signals of the said subject and electrocardiogram signals and thereby to obtain heartbeat wave forms by applying inverse transfer function of the said transfer characteristic to ballistocardiogram wave forms or bio-vibration signals of the said subject.

In addition, the phase coherence calculation device in this invention includes A biological information acquisition means that acquires at least biological information containing both information about heartbeat of a subject and information about breathing; a breathing wave form extraction means that extracts breathing pattern from the said biological information; a heart rate interval calculation means that calculates fluctuations in heartbeat interval from the said biological information; and a phase coherence calculation means that calculates phase coherence of an instantaneous phase difference between the said breathing pattern and the said fluctuations in heartbeat interval. In the above phase coherence calculation device, the said biological information may be electrocardiogram, and the said biological information may be ballistocardiogram wave forms or bio-vibration signals. In the above phase coherence calculation device, the said biological information are desirably acquired at sampling frequency not less than 100 Hz. Furthermore, the said biological information acquisition means desirably includes a wearable sensor that can put on body of the subject, and the said wearable sensor is more desirably implemented on a wearing part that puts on a limb or head of the subject.

The stress measuring device in this invention is provided with the phase coherence calculation device. The sleep state measuring device is provided with the above phase coherence calculation device.

The heartbeat wave form extraction method in this invention, which is a method that extracts heartbeat wave forms from ballistocardiogram wave forms or bio-vibration signals of the subject, estimates transfer characteristic between ballistocardioaction from the said ballistocardiogram wave forms or bio-vibration signals and electrocardiogram signals, and obtains heartbeat wave forms by applying inverse transfer function of the said transfer characteristic to the said ballistocardiogram wave forms or bio-vibration signals. In the above heartbeat wave form extraction method, it is desirable to estimate transfer characteristic of the ballistocardioaction by cutting wave form fragment from the said ballistocardiogram wave forms or bio-vibration signals so that the fragment includes one heartbeat, and overlapping multiple said wave form fragments followed by averaging.

The heart rate interval calculation method in this invention is a method that calculates heart rate interval from ballistocardiogram wave forms or bio-vibration signals of the subject, wherein signals derived from the said ballistocardiogram wave forms or bio-vibration are passed through a high-pass filter with the lower limit frequency higher than the heartbeat frequency, and the signals after the said high-pass filter are processed to the absolute value.

The signal processing method in this invention is a signal processing method on biological information containing information related to heartbeat of the subject or biological information containing information related to breathing, wherein the upper limit frequency or lower limit frequency is determined based on the power spectrum of signal derived from the said biological information followed by processing in which the information are passed through a filter with the said upper limit frequency or lower limit frequency used as the cutoff frequency.

Effects of the Invention

The sleep state measuring device and method in this invention is capable of measuring sleep state using correlation of δ wave amplitude to phase coherence in instantaneous phase difference between instantaneous phase of fluctuations in heartbeat interval and that of breathing pattern. The phase coherence is insusceptible to breathing frequency and thus allows more accurate sleep state measurement. In addition, even one sensor can realize a key function of the sleep state measuring device, allowing the inventor to provide a less-burdensome and less-stressful device to users. Especially, a sensor for measurement of vibrations can achieve measurement without restraining the subject, allowing the inventor to provide a more simplified device to users. The phase coherence can be measured in real time, allowing measurement of onset time point of non-REM sleep time and rhythm cycle of non-REM to REM sleep, and thereby the sleep state can be identified accurately. In addition, the device measures or extracts breathing pattern at the same time so that apneic state during sleep can be also detected.

The phase coherence calculation device in this invention obtains fluctuations in heartbeat interval and breathing pattern from at least biological information containing both information about heartbeat of a subject and information about breathing and thereby calculate phase coherence. The device achieves the above calculation with one sensor, and thus it can be less-burdensome and less-stressful to users. Especially, a sensor for measurement of vibrations can achieve measurement without restraining the subject, allowing the inventor to provide a more simplified device to users. Measurement of phase coherence can facilitate examination of the mental stress state and sleep state of a subject in real-time independent of breathing frequency.

In addition, the above device is designed to use a wearable sensor that can put on body of the subject, especially a limb or head of the subject, for example, a wearable sensor implemented on a wearing part that puts on a finger of a subject. Such sensor can achieve less-burdensome and less-stressful measurement without restraining the subject, allowing development of a more simplified device. In addition, the device is capable of measuring bio-vibration signals containing both information about heartbeat and information about breathing, and calculating biological information about heartbeat and breathing in real time. Especially, the device is capable of calculating phase coherence in instantaneous phase difference between fluctuations in heartbeat interval and breathing pattern in real time, allowing examination of the mental stress state and sleep state of a subject in real-time independent of breathing frequency.

BRIEF DESCRIPTION OF THE DRAWINGS

FIG. 4 (A) shows electrocardiogram wave forms (top) as well as extracted breathing pattern (solid underline) and measured values in the breathing pattern (dotted underline); (B) shows a graph of fluctuations in heartbeat interval; and (C) shows instantaneous phase of fluctuations in heartbeat interval (solid line) and instantaneous phase (dotted line) of breathing pattern as well as calculated phase coherence λ (bottom).

FIG. 8 (A) shows ballistocardiogram wave forms (top) and simulated electrocardiogram wave forms extracted from the ballistocardiogram wave forms (bottom); and (B) shows an average transfer characteristic determined from the ballistocardiogram wave forms.

FIG. 170 shows an overview diagram of configuration of the bracelet-type bio-vibration signal measuring device in Operating form 2.

DESCRIPTION OF EMBODIMENTS OF THE INVENTION

[Sleep State Measuring Device and Method]

Sleep states are classified based on brain waves and eye movement pattern. Brain waves are measured with electroencephalogram ("EEG") in which temporal changes in electrical activity occurring in the brain are recorded. When an awake subject is at rest, α waves (frequency, 8 to 13 Hz; amplitude, approximately 50 μV) are dominant, but when a mental activity takes place, α waves are suppressed, and β waves with a smaller amplitude (frequency, not less than 14 Hz; amplitude, mainly not more than approximately 30 μV) appear. At a shallow sleep state, the percentage of α waves gradually decreases, and θ waves (frequency, 4 to 8 Hz) appear. At a deep sleep state, δ waves (frequency, 1 to 4 Hz) are dominant. Because the frequency of β waves is faster than that of α waves, the former is called fast waves in some cases. In addition, brain waves slower than α waves are called slow waves in some cases, and θ waves and δ waves are classified into slow waves.

Sleep is largely classified into REM sleep or non-REM sleep, and the non-REM sleep is further divided into 4 stages ranging from Stage I to Stage IV. Stage I (relaxed wakefulness, beginning of sleep) is a dozing state, in which α waves are losing rhythm and gradually becoming flat. Stage II is characterized by a deeper sleep state than that at Stage I, in which sleep spindles (SPINDLE) and K-complexes appear. Stage III is characterized by a substantially deep sleep state, in which δ waves account for not less than 20% and less than 50% of brain waves. Stage IV is characterized by a deepest sleep state, in which δ waves account for not less than 50%. In Stages III and IV of non-REM sleep, slow waves constitute a large percentage of brain waves, and thus sleep at these stages is also called slow wave sleep. REM sleep, on the other hand, is characterized by brain waves in a low amplitude fast wave pattern similar to those of an awake subject but by a deep sleep state that requires stronger stimulation for awakening than the slow wave sleep state, and associated with rapid eye movement. The sleep state is usually changed at a cycle (sleep cycle) of approximately 90 minutes; it is gradually deepened starting with Stage I of non-REM sleep and then changed to a shallow sleep state followed by transition into REM sleep. The sleep state, however, is affected by sleeping time; in the beginning of sleep, non-REM sleep is dominant, and in a late phase of sleep, REM sleep is mostly dominant. As described above, in an electroencephalogram, δ waves at frequency of 1 to 4 Hz appear during slow wave sleep, and thus δ waves can be used as an indicator of sleep depth.

Figure 1:
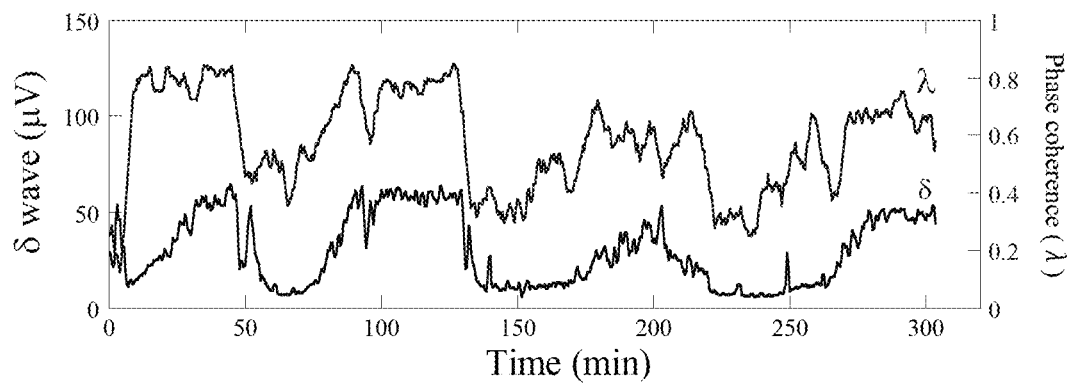
FIG. 1 The figure shows temporal changes in δ wave amplitude in an electroencephalogram during sleep and phase coherence during sleep.

These inventors have discovered that phase coherence of instantaneous phase difference between fluctuations in heartbeat interval and breathing pattern (hereinafter referred to as "phase coherence") during sleep is correlated with δ waves in an electroencephalogram during sleep; and have invented that the sleep state can be determined by measuring the phase coherence. FIG. 1 shows temporal changes in δ wave amplitude (δ) in an electroencephalogram and phase coherence (λ) during sleep of a subject. In FIG. 1, as δ wave amplitude increases, the phase coherence (λ) is becoming approximate to 1; and as δ wave amplitude decreases, the phase coherence (λ) tends to become approximate to 0; and thus correlation of these parameters is confirmed. The mean correlation coefficient between λ and δ waves from measurement in 11 subjects was 0.53 with the standard deviation of 0.10. In addition, a change in λ occurred 11.6 minutes before a change in δ wave on average.

The phase coherence represents an extent of dispersion of phase difference between 2 signals. In this invention, it represents an extent of dispersion of phase difference between fluctuations in heartbeat interval derived from breathing and breathing pattern. The heart rate interval is shortened during inspiration and extended during expiration according to respiratory sinus arrhythmia (RSA). Due to impact of breathing, therefore, the heart rate interval varies in cycles similar to those of breathing pattern. According to the above discovery, a dispersion of phase difference between fluctuations in heartbeat interval and breathing pattern is small during deep sleep (δ wave dominant) (phase coherence approximates to 1), while the dispersion increases as the sleep depth becomes shallow (phase coherence approximates to 0).

For the phase coherence, instantaneous phase difference between fluctuations in heartbeat interval and breathing pattern in the same time series can be calculated from information about each heart rate interval and breathing pattern. The information about each heart rate interval can be obtained from biological information containing information about heartbeat. Biological information containing information about heartbeat may be acquired, for example, from electrocardiogram in which temporal changes in action potential associated with heartbeat are measured, ballistocardiogram wave forms in which temporal changes in vibrations associated with heartbeat are measured, and bio-vibration signals in which temporal changes in vibrations of a subject (including ballistocardioaction) are measured. In addition, breathing pattern may be acquired from biological information containing information about breathing pattern. Biological information containing breathing pattern may be acquired, for example, from measured values on air flow caused by breathing, ones on changes in thoracic mechanical impedance associated with breathing, ones on changes in temperature caused by breathing, ones on abdomen movement associated with breathing movement, electrocardiogram, ballistocardiogram wave forms, and bio-vibration signals. Electrocardiography is designed to measure temporal changes in myocardial action potential associated with heartbeat through the body surface, but it also measures temporal changes in body surface potential associated with breathing. The electrocardiogram therefore presents biological information containing both information about heartbeat and information about breathing pattern. Ballistocardiograhy is designed to measure temporal changes in vibrations associated with heartbeat, but it also measures temporal changes in vibrations associated with breathing. The ballistocardiogram wave forms present biological information containing both information about heartbeat and information about breathing pattern. Bio-vibration signals are obtained from vibrations of a subject, which include vibrations associated with heartbeat and ones associated with breathing, and thus present biological information containing both information about heartbeat and information about breathing pattern. Information about heartbeat or information about breathing pattern required for calculation of phase coherence can be extracted from electrocardiogram, ballistocardiogram wave forms, or bio-vibration signals alone, or in combination. The extracted information about heartbeat or information about breathing pattern can be used in calculation of phase coherence.

Phase coherence is calculated as follows: instantaneous phase ψh (t) of fluctuations in heartbeat interval associated with breathing and instantaneous phase ψr (t) of breathing pattern are calculated; and the difference (instantaneous phase difference) between the above values is calculated; and the calculated instantaneous phase difference is then used in calculation of the phase coherence. The instantaneous phase ψh (t) of fluctuations in heartbeat interval is calculated as follows: temporal changes in fluctuations in heartbeat interval (S (t)) associated with breathing are calculated from data on heart rate interval; and the temporal changes in fluctuations in heartbeat interval (S (t)) are converted into analyticsignals by Hilbert transformation as provided in Equation (2) below. Where, in Equations (2) and (3), H [ . . . ] is Hilbert variable, and P.V. stands for Cauchy's principal value.

[Equation 2]

$$H[S(t)] = \frac{1}{\pi} P \cdot V \cdot \int_{-\infty}^{\infty} \frac{S(\tau)}{t-\tau} d\tau, \psi_n(t) = \tan^{-1} \frac{H[S(t)]}{S(t)} \quad (2)$$

In addition, instantaneous phase ψr (t) of breathing pattern can be calculated as follows: temporal changes in breathing pattern (R (t)) are calculated from information about breathing pattern; and the temporal changes in breathing pattern (R (t)) are converted by Hilbert transformation as provided in Equation (3) below.

[Equation 3]

$$H[R(t)] = \frac{1}{\pi} P \cdot V \cdot \int_{-\infty}^{\infty} \frac{R(\tau)}{t-\tau} d\tau, \psi_r(t) = \tan^{-1} \frac{H[R(t)]}{R(t)} \quad (3)$$

The instantaneous phase difference Ψ (t) can be calculated according to Equation (4) below, using instantaneous phase of fluctuations in heartbeat interval ψh (t) and that of breathing pattern ψr (t) calculated according to Equations (2) and (3).

$$\Psi(t)=\psi h(t)-\psi r(t)+2N\pi \quad (4)$$

Where, N is an appropriate integer to satisfy −π≤Ψ≤π.

Then, phase coherence at time tk can be calculated according to Equation (1) below. N in Equation (1) stands for number of data samples to obtain the mean.

[Equation 4]

$$\lambda(t_k) = \left| \frac{1}{N} \sum_{j=k-N/2}^{k+N/2} e^{i\Psi(t_j)} \right| \quad (1)$$

Figure 2:
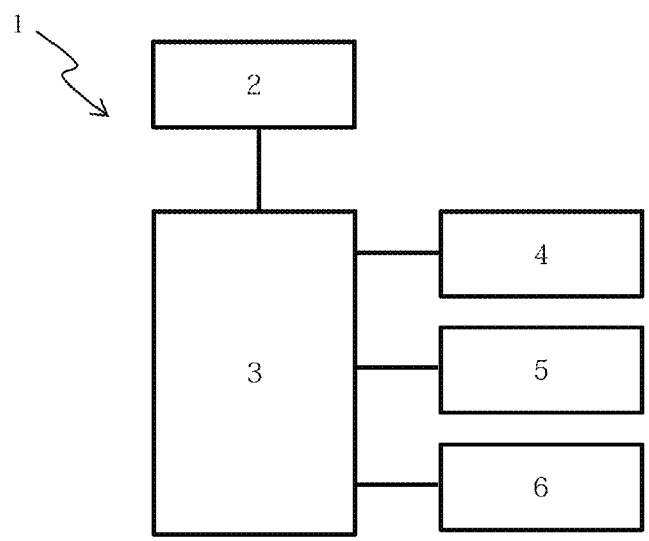
FIG. 2 The figure shows an overview block diagram of the sleep state measuring device.

As shown in FIG. 2, the sleep state measuring device 1 using phase coherence is at least provided with the information acquisition part 2 and information processing part 3. Furthermore, the sleep state measuring device 1 may be provided with the operation part 4, output part 5, and memory part 6.

The information acquisition part 2 acquires information required for calculation of phase coherence. It may have configuration including a sensor for measurement of a subject and an input part that inputs information from the sensor in a wired or wireless fashion or an input part that can input information from the other record medium with the measurement information recorded in a wired or wireless fashion. That is, the information acquisition part 2 is at least provided with an input part that input the information, or may be provided with the input part and a sensor for measurement of biological information in which both are connected in a wired or wireless fashion. If a sensor measures biological information, the sampling frequency is desirably not less than 100 Hz.

The information processing part 3 processes input information and, for example, may use processing function of a central processing unit (CPU) of the computer. In addition, the information processing may be achieved in the analog circuit, not necessarily in the digital circuit. For example, if frequency filter is performed as a part of information processing, it may be achieved with an analog filter, such as low-pass filter (LPF) and high-pass filter (HPF), consisting of condenser, resistance, and operational amplifier, or with a digital filter in which filtering is performed with the processing function of CPU. The information processing part 3 may include both digital circuit and analog circuit depending on the type of information processing. The input information in an analog format, where applicable, may be converted into digital signals through analog-digital conversion circuit. In the information processing part 3, appropriate functions or processing abilities differ depending on the input information, but at least it has a phase coherence calculation function by which phase coherence is calculated from instantaneous phase difference between fluctuations in heartbeat interval and fluctuations in heartbeat interval. In addition, a device with the phase coherence calculation function is called "phase coherence calculation device." The sleep state measuring device 1 in this invention is also classified as a phase coherence calculation device.

To calculate phase coherence, for example, the following information may be input. A) The information acquisition part 2 receives instantaneous phase difference between fluctuations in heartbeat interval and breathing pattern in the same time series as input information; and the information processing part 3 calculates phase coherence from the input instantaneous phase difference with the phase coherence calculation function. B) The information acquisition part 2 receives instantaneous phase of fluctuations in heartbeat interval and that of breathing pattern in the same time series as input information; and the information processing part 3 which has an instantaneous phase difference calculation function to calculate the instantaneous phase difference between the above two parameter values calculates the instantaneous phase difference with the concerned function, and then calculates phase coherence from the calculated instantaneous phase difference with the phase coherence calculation function. C) The information acquisition part 2 receives fluctuations in heartbeat interval and breathing pattern in the same time series as input information; and the information processing part 3 which has an instantaneous phase calculation function calculates instantaneous phase of fluctuations in heartbeat interval and that of breathing pattern with the concerned function, and then calculates phase coherence from the calculated instantaneous phases with the instantaneous phase difference calculation function and phase coherence calculation function. D) The information acquisition part 2 receives biological information containing information about heartbeat and biological information containing information about breathing as the input information; and the information processing part 3 which has heart rate interval and breathing pattern calculation functions calculates fluctuations in heartbeat interval from the biological information containing information about heartbeat with the heart rate interval calculation function and breathing pattern from the biological information containing information about breathing pattern with the breathing pattern calculation function, and then perform processing as with the above C). E) The information acquisition part 2 receives biological information containing both information about heartbeat and about breathing as the input information; and the information processing part 3 which has a function to detect or extract information about heartbeat or about breathing pattern in the concerned biological information may perform the subsequent processing using the detected or extracted information about heartbeat or breathing pattern.

Furthermore, the information processing part 3 may have an assessment function to assess sleep state based on the calculated phase coherence. In the assessment function, for example, if the calculated phase coherence is larger than the threshold, the sleep state may be assessed as a deep state; or if it is smaller than the threshold, the sleep state may be assessed as a shallow state; the sleep quality may be evaluated based on the duration in which the phase coherence remains higher than the threshold; or the sleep quality may be evaluated based on the cycle of fluctuations of the phase coherence. The threshold may be a predetermined value, be specified based on previously calculated phase coherence values in the measurement subject, or be set at multiple levels for step-wise evaluation of the sleep quality. Furthermore, the information processing part 3 can assess breathing state during sleep with an assessment function. For example, depending on the breathing pattern acquisition method, but with any acquisition method, for central sleep apnea (apnea resulted from discontinuation of breathing movement due to abnormality in the respiratory center in the brain), non-breathing state can be found based on a failure of detection of the breathing pattern due to discontinuation of the breathing movement. Furthermore, if the breathing pattern is acquired through measurement of the air flow caused by breathing, discontinuation of breathing-related air flow results in a failure of detection of the breathing pattern, and thus not only central sleep apnea but also obstructive sleep apnea (apnea caused by airway obstruction, but with breathing movement) can be found.

The operation part 4 is provided with operation terminals such as switch, touch panel, button, knob, keyboard, mouse, and voice input microphone so that users can operate the sleep state measuring device 1. The operation part 4 may be provided with a display to show details of operations. The output part 5 may output the calculated phase coherence, output biological information other than phase coherence, or output sleep state judged by the assessment function. The output part 5 can use a display that shows results in image, a printer that outputs results in paper, a speaker that outputs results in voice, and wired or wireless output terminal that outputs results as electronic information. In addition, a display that serves as the output part 5 may also function as a touch panel or display that shows details of operations in the operation part 4. The memory part 6 can capture information acquired in the information acquisition part 2, calculation results in the information processing part 3, and assessment results obtained with the assessment function.

Figure 3:
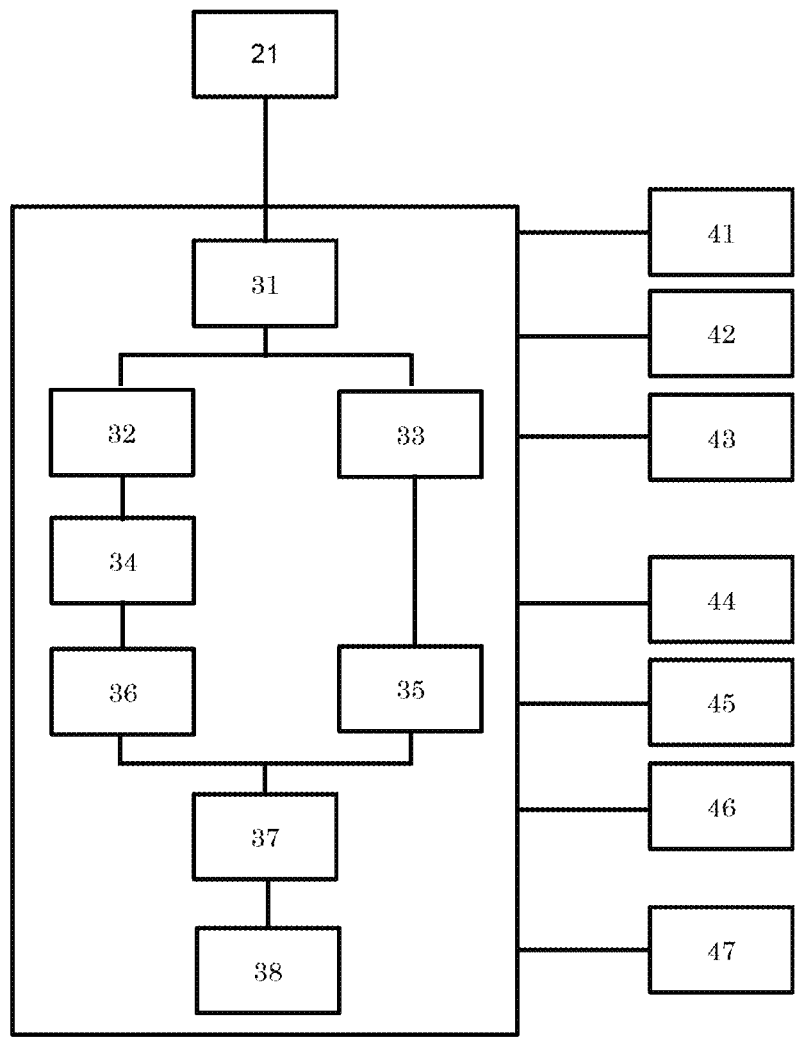
FIG. 3 The figure shows one operating form of the sleep state measuring device.

FIG. 3 shows an example of the sleep state measuring device 1. The sleep state measuring device 1 has the sensor 21, analog-digital conversion circuit 31, heartbeat extraction means 32, breathing wave form extraction means 33, heart rate interval calculation means 34, Hilbert transformation filters 35, 36, instantaneous phase difference calculation means 37, phase coherence calculation means 38, operation button 41, touch panel 42, voice input microphone 43, display 44, wireless communication means 45, speaker 46, and recording device 47.

The sensor 21 detects biological information containing information about heartbeat and biological information containing information about breathing. Examples of the above unit that detects biological information containing information about heartbeat may include a sensor for electrocardiography and one for measurement of vibrations, and ones of the above unit that detects biological information containing information about breathing may include a sensor for electrocardiography, one for measurement of vibrations, and breathing sensor. Although FIG. 3 includes one sensor, multiple types of sensors may be included. A sensor for measurement of electrocardiogram or vibrations can detect signals containing both biological information about heartbeat and biological information about breathing. One sensor can detect both signals, but an additional sensor may be used to detect either item of biological information. For a sensor for measurement of electrocardiogram, dedicated electronic circuits are desirably affixed to the chest of the body using disposable electrodes, which measure electrocardiogram wave forms. Either unipolar or bipolar leads may be used for leading.

In addition, a sensor for measurement of vibrations may be either contact or non-contact type. A contact-type sensor for measurement of vibrations can be placed in direct or indirect contact with a subject to detect ballistocardiogram wave forms or bio-vibration signals. A contact type sensor for measurement of vibrations to detect ballistocardiogram wave forms or bio-vibration signals is placed directly on various subjects that generate vibrations or in the vicinity of such subjects. It is only required to detect vibrations generated by a subject and output electric signals. For a sensor for measurement of vibrations, a piezoelectric element is desirably used as a piezoelectric sensor, but the other sensors such as a polymer piezoelectric element (polyolefin material) may be used. A material for the piezoelectric element may be, for example, porous polypropylene electret film (electro mechanical film, EMFI), polyvinylidene difluoride film (PVDF), poly[(vinylidenefluoride-co-trifluoroethylene] (P(VDF-tRFE)), or poly[(vinylidenefluoride-co-tetrafluoroethylene] (P(VDF-tFE)). The piezoelectric sensor is desirably in a film form. Furthermore, the piezoelectric sensor is desirable, because it is capable of acquiring ballistocardiogram wave forms or bio-vibration signals without restraining the subject, allowing measurement in a more stress-free state. The piezoelectric sensor, however, may be used as a wearable sensor attached to a wristband, belt, watch, ring, or headband. In addition, the other types of sensors for measurement of vibrations may be used to acquire ballistocardiogram wave forms or bio-vibration signals: for example, a highly sensitive accelerometry sensor may be attached in contact with the body like a watch or portable terminal; an accelerometry sensor may be integrated in a part of a bed or chair; and a pressure sensor that detects changes in air or liquid pressure in a tube may be used. Furthermore, as a sensor for measurement of vibrations, a non-contact type sensor that can acquire ballistocardiogram wave forms or bio-vibration signals in a non-contact fashion through signal transmission of microwaves, etc. may be used. Ballistocardiogram wave forms or bio-vibration signals acquired from the following data may be used: data obtained with a microwave Doppler sensor; data obtained with receiving waves that facilitate determination of a distance from the object based on reflection delay time of ultrawide band (UWB) impulses; data obtained with electromagnetic waves other than microwaves; data obtained with reflected or transmitted beam using LED light; and data obtained with reflected waves using ultrasonic waves. These sensors using microwaves, etc. can be downsized and capable of acquiring signals in a non-contact and non-restraint manner under a remote operating condition. In addition, accelerometry sensors can be downsized as well.

A breathing sensor measures temporal changes in breathing pattern based on, for examples, measured values on air flow caused by breathing, ones on thoracic mechanical impedance changes associated with breathing, ones on temperature changes caused by breathing, ones on abdomen movement associated with breathing movement. Signals detected with the sensor 21 are input into the analog-digital conversion circuit 31 of the sleep state measuring device 1 in a wired or wireless fashion. The top graph in FIG. 4 (A) shows electrocardiogram wave forms measured with a sensor for measurement of electrocardiogram.

The analog-digital conversion circuit 31 is a circuit that converts analog signals from the sensor 21 into digital signals. The analog-digital conversion circuit 31 may be placed in the sensor 21, or it may not be placed, if the sensor 21 detects digital signals. In addition, analog signals from the sensor 21 may be processed by filtering, etc. before conversion into digital signals with the analog-digital conversion circuit 31.

The heartbeat extraction means 32 is a means that extracts signals related to heartbeats from signals detected with the sensor 21. For this means, processing appropriate for the type of the sensor or input signals is selected. If input data are electrocardiogram wave forms or ballistocardiogram wave forms, it is usually desirable to perform processing to remove breathing components, because the above input data are affected by breathing. If there is no problem in calculation of heart rate interval, the heartbeat extraction means may not be used. In addition, if input data are bio-vibration signals, it is desirable to perform processing to remove noise vibrations caused by breathing, body movements, vocalization, and external environment, because such signals include such vibrations other than ones based on ballistocardioaction caused by heart beating. The following processing may be performed: for example, strength of the electrocardiogram wave forms or vibration signals is raised to the Nth power (N is an integer not less than 2, and if N is odd, the absolute value is used) for accentuation processing followed by band-pass filtering (BPF). The BPF of the heartbeat extraction means 32 is desirably performed with the lower limit frequency not less than 0.5, 0.6, 0.7, 0.8, 0.9, or 1 Hz and the upper limit frequency not more than 10, 8, 6, 5, or 3 Hz. The desirable pass band ranges from any of the above lower limit frequencies to any of the above upper limit frequencies. The lower limit frequency of the heartbeat extraction means 32 may be the same as the upper limit frequency of the breathing wave form extraction means 33, or lower than the upper limit frequency of the breathing wave form extraction means 33, even which results in superimposition of a part of the pass band of the heartbeat extraction means 32 on that of the breathing wave form extraction means 33. For the heart rate interval extraction method, it is desirable to determine the upper limit frequency or lower limit frequency of the filtering based on the acquired ballistocardiogram wave forms or bio-vibration signals. Furthermore, it is more desirable to determine the upper limit frequency or lower limit frequency of the filtering based on the acquired ballistocardiogram wave forms or bio-vibration signals at regular or irregular intervals. For example, the pass frequency may be determined as follows: firstly, power spectrum is determined from ballistocardiogram wave forms or bio-vibration signals, or pre-processed signals thereof (signals obtained after noise removal or accentuation processing on the above signals) (signals derived from the ballistocardiogram wave forms or bio-vibration signals); the initial peak is identified by scanning the power spectral density starting from not less than 0.5 Hz; the frequency band on the low frequency side and/or high frequency side is determined based on frequencies where the peak signal is decreased to a specified threshold (for example, half-width height); and the above band may be used as the pass frequency. The power spectrum can be determined, for example, by Fourier transformation. Signal processing using the filtering with the upper limit frequency or lower limit frequency determined from the acquired ballistocardiogram wave forms or bio-vibration signal, as the above, achieved establishment of the filter that not only corresponds to biological information specific to the body of a subject and conditions at the time of acquisition such as posture, physical condition, and environment but also accommodates individual differences and conditions at the time of acquisition. Thereby, phase coherence has been calculated in real time. In addition, if a breathing sensor is used in a part of the sensor 21, signals from the breathing sensor would not have to be input in the heartbeat extraction means 32.

Furthermore, heart rate interval can be calculated from ballistocardiogram wave forms as follows: ballistocardiogram wave forms are passed through a high-pass filter (HPF) with the lower limit frequency higher than heartbeat frequency; envelope signals of post-HPF signals, obtained using their absolute values, lead to identification of a peak of each heartbeat in the ballistocardiogram wave forms; and finally the heart rate interval can be determined from the peak value or the starting point of the heartbeat peak. Usual heartbeat frequency is approximately 3 Hz at the maximum, but the lower limit frequency for HPF is desirably not less than 5 Hz, that is, 10, 20, 30, or 40 Hz may be acceptable. The phase coherence ($\lambda$) value obtained from fluctuations in heartbeat interval calculated by this signal processing method was remarkably similar to the phase coherence ($\lambda$) value determined from the electrocardiogram wave forms. The post-HPF signals of which absolute values are used in the processing method are preferably subjected to BPF (or LPF) with the pass frequency determined from the above power spectrum. Furthermore, pre-processing of noise removal may be performed before HPF processing. Bio-vibration signals (containing ballistocardiogram wave forms) include vibration wave forms associated with heartbeat. It is conventionally difficult to identify each beating interval, equivalent to RRI, from the raw wave forms, because superimposition of a vibration component associated with breathing movement on the heartbeat component, if any, would destabilize the wave forms. In this method, breathing frequency component that is superimposed on the heartbeat fundamental frequency component is removed in advance, and then the high frequency vibration component originated from heartbeat is used to determine the beating interval, which is more accurate than that without the prior removal. The method achieves accurate detection of respiratory sinus arrhythmia, fluctuations in heartbeat interval. As a result, the calculated phase coherence almost agrees with that determined from electrocardiogram and measured breathing data.

Figure 5:
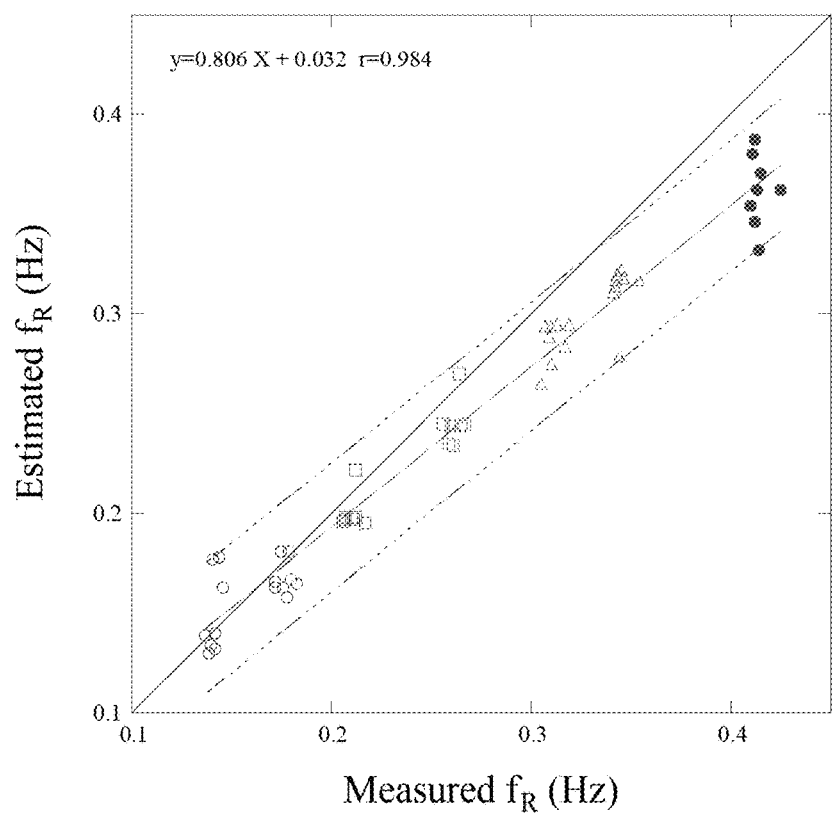
FIG. 5 The figure shows correlation of measured breathing frequency to estimated breathing frequency extracted from electrocardiograms at different breathing rates of 8, 10, 12, 15, 18, 20, and 24/min.
Figure 6:
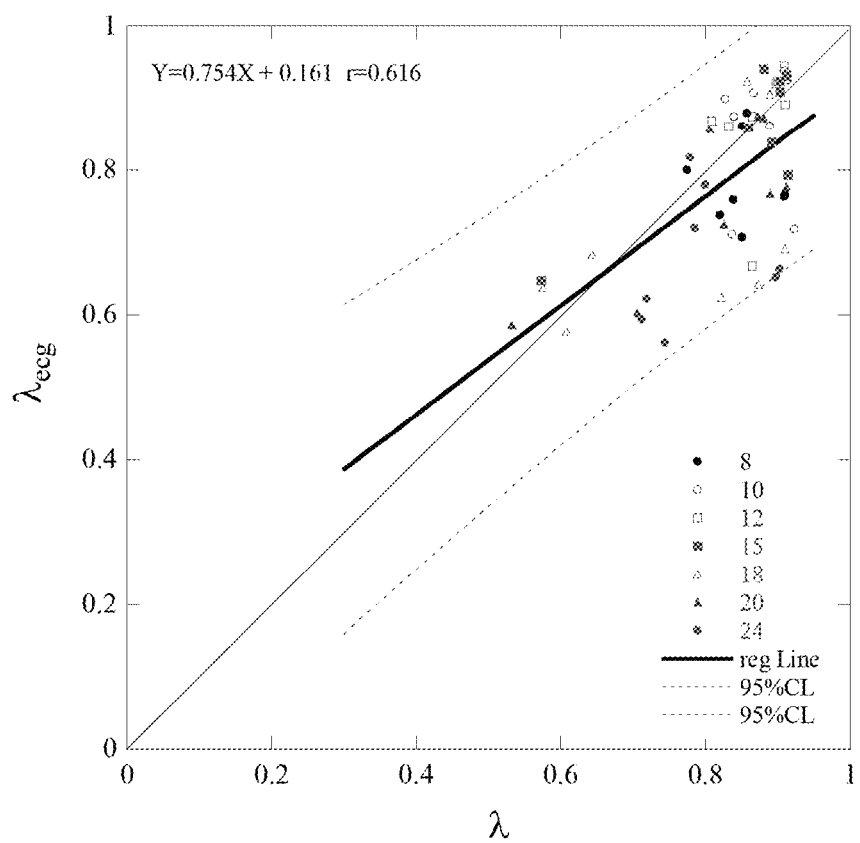
FIG. 6 The figure shows correlation of phase coherence λ calculated using measured breathing frequency to phase coherence λecg calculated using estimated breathing frequency at different breathing rates of 8, 10, 12, 15, 18, 20, and 24/min.

The breathing wave form extraction means 33 is a means that extracts signals related to breathing pattern from signals detected with the sensor 21. According to a type of the sensor or input signals, appropriate processing is selected. If the sensor 21 has a function of breathing sensor that measures breathing pattern, the breathing wave form extraction means 33 may not be placed, or the breathing wave form extraction means 33 may perform processing to remove noise signals. When signals related to breathing pattern are extracted from electrocardiogram wave forms, ballistocardiogram wave forms, or bio-vibration signals, the following processing may be performed: for example, strength of the electrocardiogram wave forms or vibration signals is raised to the Nth power (N is an integer not less than 2, and if N is odd, the absolute value is used) for accentuation processing followed by low-pass filtering (LPF) with the pass band of the frequency not more than 0.5 Hz. The LPF cutoff frequency of the breathing wave form extraction means 33 may be 0.3, 0.4, 0.6, 0.7, or 0.8 Hz. In addition, the cutoff frequency of the breathing wave form extraction means 33 may be the same as the lower limit frequency of the heartbeat extraction means 32 or higher than the lower limit frequency, even which results in superimposition of a part of the pass band. For the breathing wave form extraction method, it is desirable to determine the upper limit frequency or lower limit frequency of the filtering based on the acquired electrocardiogram wave forms, ballistocardiogram wave forms, or bio-vibration signals. Furthermore, it is more desirable to determine the upper limit frequency or lower limit frequency of the filtering based on the acquired ballistocardiogram wave forms or bio-vibration signals at regular or irregular intervals. The cutoff frequency may be determined as follows: firstly, power spectrum is determined from electrocardiogram wave forms, ballistocardiogram wave forms, or bio-vibration signals, or pre-processed signals thereof (signals obtained after noise removal or accentuation processing on the above signals); the initial peak is identified by scanning the power spectral density starting from low frequency side; and the frequency on the high frequency side where the peak signal is decreased to a specified threshold (for example, half-width height) may be used as cutoff frequency. Signal processing using the filtering with the upper limit frequency or lower limit frequency determined from the acquired electrocardiogram wave forms, ballistocardiogram wave forms, or bio-vibration signals, as the above, achieved establishment of the filter that not only corresponds to biological information specific to the body of a subject and conditions at the time of acquisition such as posture, physical condition, and environment but also accommodates individual differences and conditions at the time of acquisition. Thereby, phase coherence has been calculated in real time. In addition, BPF may be used for filtering in place of LPF. In this case, the lower limit frequency of BPF is only required to be sufficiently low; for example, it may be set at 0.1 Hz. The graph at the bottom of FIG. 4 (A) shows breathing patterns of which one in the solid line is extracted from electrocardiogram wave forms, and the other one in the dotted line is depicted according to the measured airflow caused by breathing. The graph at the bottom of FIG. 4 (A) demonstrates that cycles in the breathing pattern even extracted from electrocardiogram wave forms agree with the measured values FIG. 5 shows correlation of measured breathing frequency to estimated breathing frequency extracted from electrocardiograms in 8 subjects at different breathing rates of 8, 10, 12, 15, 18, 20, and 24/min. The dotted line shows 95% confidence interval of breathing frequency. At the breathing frequency exceeding approximately 0.4 Hz, 95% confidence interval deviates from the identity line, leading to underestimation, but at the frequency less than 0.4 Hz, the breathing frequency can be estimated at the precision not less than 90%. FIG. 6 shows correlation of phase coherence $\lambda$ calculated using measured breathing frequency to phase coherence $\lambda ecg$ calculated using estimated breathing frequency in FIG. 5. At the breathing frequency up to 0.33 Hz (20/min), phase coherence can be determined at the precision not less than 90%.

The heart rate interval calculation means 34 receives signals from the heartbeat extraction means 32 to calculate heartbeat interval. To measure a heartbeat interval, for example, a distance of P, R, t, or U waves in electrocardiogram may be used, but one from an R wave to the next R wave is desirably measured, because R waves have a sharp peak. Even when signals about heartbeat extracted from ballistocardiogram wave forms or bio-vibration signals are used, an interval of wave forms corresponding to R waves with sharp peak is desirably measured. FIG. 4 (B) shows fluctuations in heartbeat interval calculated from the electrocardiogram in FIG. 4 (A), and heart rate interval (ms) and time (s) are plotted on the vertical and horizontal axes, respectively. FIG. 4 (B) demonstrates that the heart rate interval varied at a consistent cycle. In addition, amplitude of respiratory sinus arrhythmia (RSA) may be used as an indicator for assessment of mental stress. As described below, the RSA amplitude changes in response to breathing frequency, and thus it is desirably used for assessment in combination with phase coherence as an auxiliary or additional indicator. In addition, the heart rate interval calculation means 34 may calculate heartbeat interval directly from biological information containing information about heartbeat. In this case, the heart rate interval calculation means 34 may include a function of the heartbeat extraction means 32, or depending on the signal processing method, heartbeat interval can be calculated directly from biological information containing information about heartbeat without the heartbeat extraction means 32.

The Hilbert transformation filter 35 outputs instantaneous phase and instantaneous amplitude for fluctuations in heartbeat interval. The Hilbert transformation filter 36 outputs instantaneous phase and instantaneous amplitude for breathing pattern. For Hilbert transformation, 90-degree phase difference wave separator may be achieved with analog circuit, or a finite impulse response digital filter may be used. The Hilbert-transformed signals and actual signals are combined to generate analytic signals, in which the ratio of the actual part to the imaginary part can facilitate determination of instantaneous phase. The graph at the top of FIG. 4 (C) shows instantaneous phase of fluctuations in heartbeat interval in the solid line and that of breathing pattern in the dotted line. The phase (radian) and time (s) are plotted on the vertical and horizontal axes, respectively.

The instantaneous phase difference calculation means 37 calculates phase difference (instantaneous phase difference) between instantaneous phase of fluctuations in heartbeat interval and that of breathing pattern, and outputs the results into the phase coherence calculation means 38. The phase coherence calculation means 38 calculates phase coherence using instantaneous phase difference between fluctuations in heartbeat interval and breathing pattern, as described above. Data used to determine phase coherence should be subjected to calculation with a window size of at least 1 breathing cycle. The graph at the bottom of FIG. 4 (C) shows calculated phase coherence $\lambda$. FIG. 4 (C) shows that the phase coherence is always close to 1 with relatively small dispersion. The sleep state measuring device 1 may have a function to assess sleep state from further calculated phase coherence λ.

The operation button 41, touch panel 42, and voice input microphone 43 are input means for users to operate the sleep state measuring device 1. They can make the sleep state measuring device 1 operate or output necessary information. The display 44 and speaker 46 can be used as output means that output heartbeat, breathing pattern, respiratory sinus arrhythmia, and phase coherence λ as well as sleep state estimated from the phase coherence λ. The wireless communication means 45 may be used as an output means of calculated phase coherence λ and sleep state or as an input means that input signals from the sensor 20. In addition, the sleep state may be output in voice. In the recording device 47, input information, programs of various means, and measurement results are recorded.

The sleep state measuring device 1 may be achieved with a portable terminal (for example, cellular phone, smart phone) and a sensor. The sensor transmits the detected signals to the portable terminal as follows: for example, an electrocardiogram sensor is provided with A/D conversion circuit and wireless communication function; signals detected with the sensor are converted into digital signals through the A/D conversion circuit; and the digital signals are transmitted to the portable terminal through the wireless communication function. For the wireless communication function, for example, Bluetooth (trademark) or Wi-fi (trademark) is desirable.

The sleep state measuring device 1 in this invention can measure sleep state using the finding that amplitude of δ wave is correlated with phase coherence of instantaneous phase difference between fluctuations in heartbeat interval and breathing pattern. The phase coherence, as described below, is insusceptible to breathing frequency, allowing more accurate sleep state measurement. In addition, even one sensor can realize a key function of the sleep state measuring device 1, allowing the inventor to provide a less-burdensome and less-stressful device to users. Especially, a sensor for measurement of vibrations can achieve measurement without restraining the subject, allowing the inventor to provide a more simplified device to users. The phase coherence can be measured in real time, allowing measurement of onset time point of non-REM sleep time and rhythm cycle of non-REM to REM sleep, and thereby the sleep state can be identified accurately. In addition, the device measures or extracts breathing pattern at the same time so that apneic state during sleep can be also detected. Furthermore, size of respiratory sinus arrhythmia in a subject can be measured as an auxiliary assessment indicator of sleep state.

[Phase Coherence Calculation Device and Method]

The phase coherence can be used for evaluation of not only sleep state but also mental stress. Especially, the phase coherence calculation device explained in this operating form acquires fluctuations in heartbeat interval and breathing pattern from biological information at least containing information about heartbeat and information about breathing of a subject, and calculates phase coherence.

Figure 7:
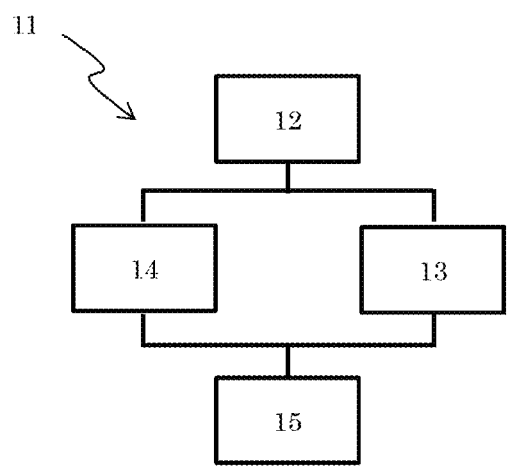
FIG. 7 The figure shows an overview block diagram of the phase coherence calculation device.

FIG. 7 shows overview block diagram of the phase coherence calculation device 11. The phase coherence calculation device 11 includes at least the biological information acquisition means 12, breathing wave form extraction means 13, heart rate interval calculation means 14, and phase coherence calculation means 15. Furthermore, the phase coherence calculation device 11 may be provided with the other means shown in FIG. 3. Of the phase coherence calculation device 11 in this operating form, the biological information acquisition means 12 acquires biological information containing both information about heartbeat and information about breathing of a subject. The biological information may be, for example, electrocardiogram, ballistocardiogram wave forms, or bio-vibration signals. The biological information acquisition means 12 may have configuration including a sensor for measurement of a subject and an input part that inputs information from the sensor in a wired or wireless fashion or an input part that can input information from the other record medium with the measurement information recorded in a wired or wireless fashion. That is, the information acquisition part 2 is provided with at least an input part that inputs information, and Where necessary it may be provided with a sensor for measurement of biological information that is connected with the input part in a wired or wireless fashion. If a sensor measures biological information, the sampling frequency is desirably not less than 100 Hz.

As explained for the above sleep state measuring device 1, fluctuations in heartbeat interval and breathing pattern can be acquired by extracting breathing pattern from electrocardiogram. To acquire ballistocardiogram wave forms or bio-vibration signals, a sensor for measurement of vibrations may be placed in contact with the body directly or in contact with a component to which vibrations of the body are transmitted (including floor, bed, chair, desk, clothing, shoe, carpet, sheet, and cover), or away from the body in a non-contact manner where applicable. The component on which the contact-type sensor for measurement of vibrations is placed may be separated from the body by multiple components. For example, a sensor for measurement of vibrations may be placed on a floor, on or under a bed mat, front or back surface of seat or back board of a chair, top or back surface of a top board of a desk, or mounted into any of the above articles. Furthermore, a sensor for measurement of vibrations may be mounted in one of the protective components attached to the feet, frame, head board, side rail, etc. of a bed; or leg, armrest, frame, etc. of a chair; or leg, batten, end rail, etc. of a desk. In addition, a sensor for measurement of vibrations may be mounted on a toilet seat or toilet bowl; it may be placed on the top or back surface, or inside of a toilet seat or toilet bowl. For example, a sensor part for measurement of vibrations may be arranged in a buffer part of the back surface of a toilet seat that is located at the joint site with a toilet bowl, or at the joint site of the top surface of a toilet bowl with a toilet seat. In addition, a sensor for measurement of vibrations, as described above, can be a piezoelectric sensor, accelerometry one, pressure one, or non-contact one.

In the case where ballistocardiogram wave forms or bio-vibration signals are acquired, information about heartbeat and information about breathing have to be separately extracted. The information about heartbeat and information about breathing can be extracted according to frequency using low-pass filter (LPF), band-pass filter (BPF), and high-pass filter (HPF). To determine further accurate heartbeat from ballistocardiogram wave forms or bio-vibration signals, the following calculation can be performed: transfer characteristic of ballistocardioaction is calculated to estimate inverse transfer function, by which wave forms equivalent to electrocardiogram are determined from ballistocardiogram wave forms or bio-vibration signals. For the inverse transfer function, transfer characteristic may be investigated by prior measurement of electrocardiogram and ballistocardiogram of a subject, but it can be estimated only from ballistocardiogram wave forms or bio-vibration signals.

Simulated electrocardiogram wave forms can be obtained as follows: ballistocardiogram wave forms with low frequency component removed is passed through Wiener filter; and the inverse transfer function and the original ballistocardiogram wave forms are subjected to superimposition and integration so that simulated ones can be obtained. In addition, heart rate interval can be calculated from ballistocardiogram wave forms as follows: ballistocardiogram wave forms are passed through a high-pass filter (HPF) with the lower limit frequency higher than heartbeat frequency; envelope signals of post-HPF signals, obtained using their absolute values, lead to identification of a peak of each heartbeat in the ballistocardiogram wave forms; and finally the heart rate interval can be determined from the peak value or the starting point of the heartbeat peak.

FIG. 8 (A) shows ballistocardiogram wave forms (top) and simulated electrocardiogram wave forms extracted from the ballistocardiogram wave forms (bottom). Firstly, in ballistocardiogram wave forms in which sharp peaks are generated periodically, time (t) of a peak is determined; on the assumption that the time (t) is time of R wave in electrocardiogram, a wave form fragment that starts at the sharp peak is cut from ballistocardiogram wave forms with a specified window size (up to the next peak), followed by superimposition. It is desirable to remove wave form fragments with large dispersion due to disagreement of the time (t) with time of R wave. The solid line in FIG. 8 (B) represents mean values as a result of superimposition of 100 wave form fragments, while the dotted line represents the standard deviation. This solid line is considered as mean transfer characteristic between electrocardiogram and ballistocardioaction. Using the inverse transfer function of the concerned transfer characteristic, simulated electrocardiogram wave forms were obtained from ballistocardiogram wave forms. As describe above, further accurate extraction can be achieved by the following calculation: transfer characteristic of ballistocardioaction is calculated to estimate inverse transfer function, by which wave forms equivalent to electrocardiogram is determined from ballistocardiogram wave forms or bio-vibration signals Especially, the phase coherence calculation device and sleep state measuring device in this invention extract fluctuations in heartbeat interval and breathing pattern, and thus it is important to determine wave forms equivalent to electrocardiogram accurately.

In addition, signals related to breathing can be extracted from ballistocardiogram wave forms, for example, by using low-pass filter (LPF) or by extracting breathing-related amplitude modulation from simulated electrocardiogram wave forms.

Figure 9:
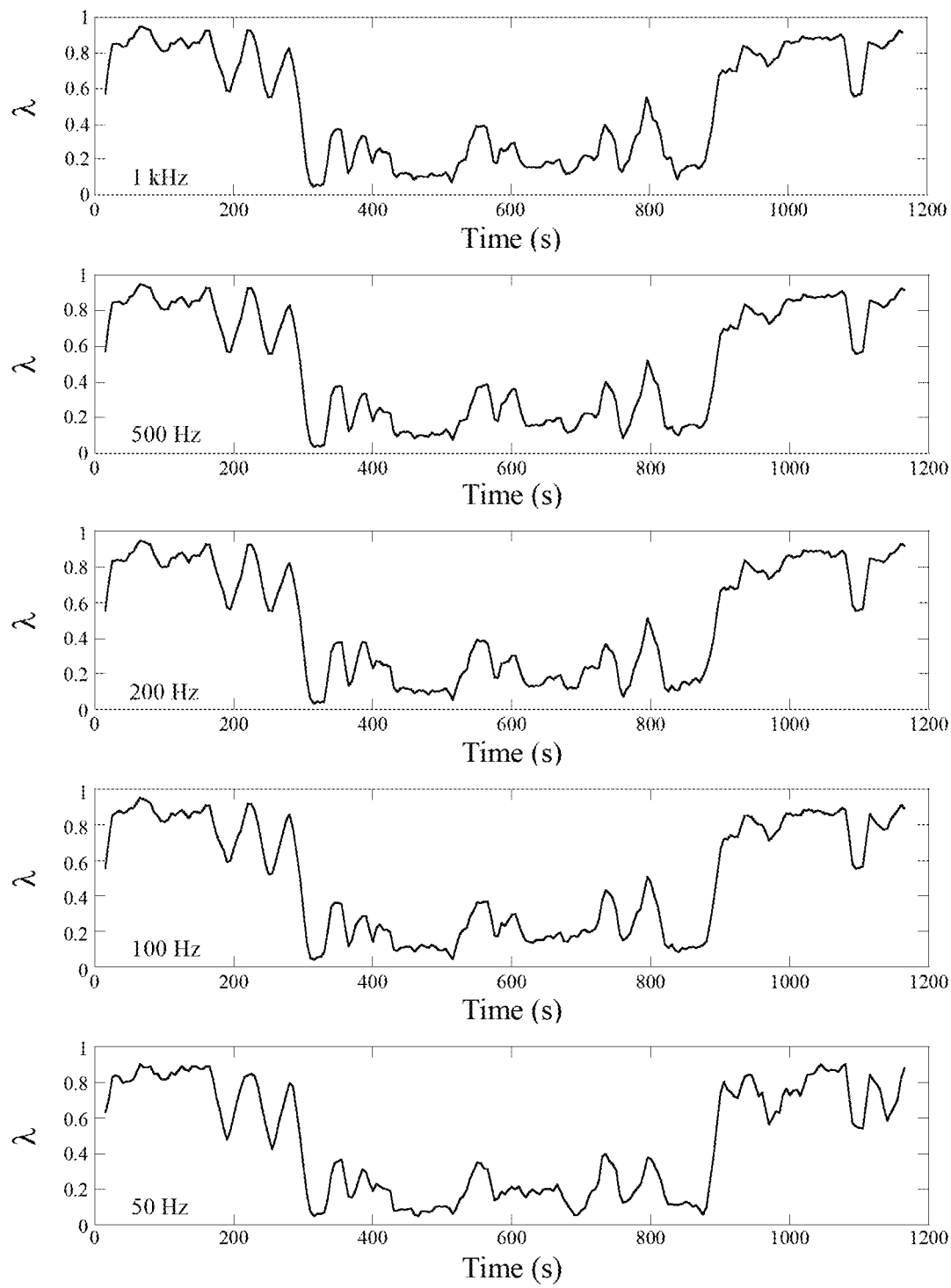
FIG. 9 The figure compares phase coherences at different sampling frequencies of 1000, 500, 200, 100, and 50 Hz for acquisition of electrocardiogram wave forms.

If a sensor measures biological information, the sampling frequency is desirably not less than 100 Hz. FIG. 9 shows compares phase coherences at different sampling frequencies of 1000, 500, 200, 100, and 50 Hz for acquisition of electrocardiogram wave forms. The root mean square error (RMSE) in comparison with phase coherence of electrocardiogram at sampling frequency of 1000 Hz is 0.028 for 500 Hz, 0.039 for 200 Hz, 0.045 for 100 Hz, and 0.109 for 50 Hz. As shown above, the sampling frequency not less than 100 Hz can give adequately precise phase coherence.

Figure 10:
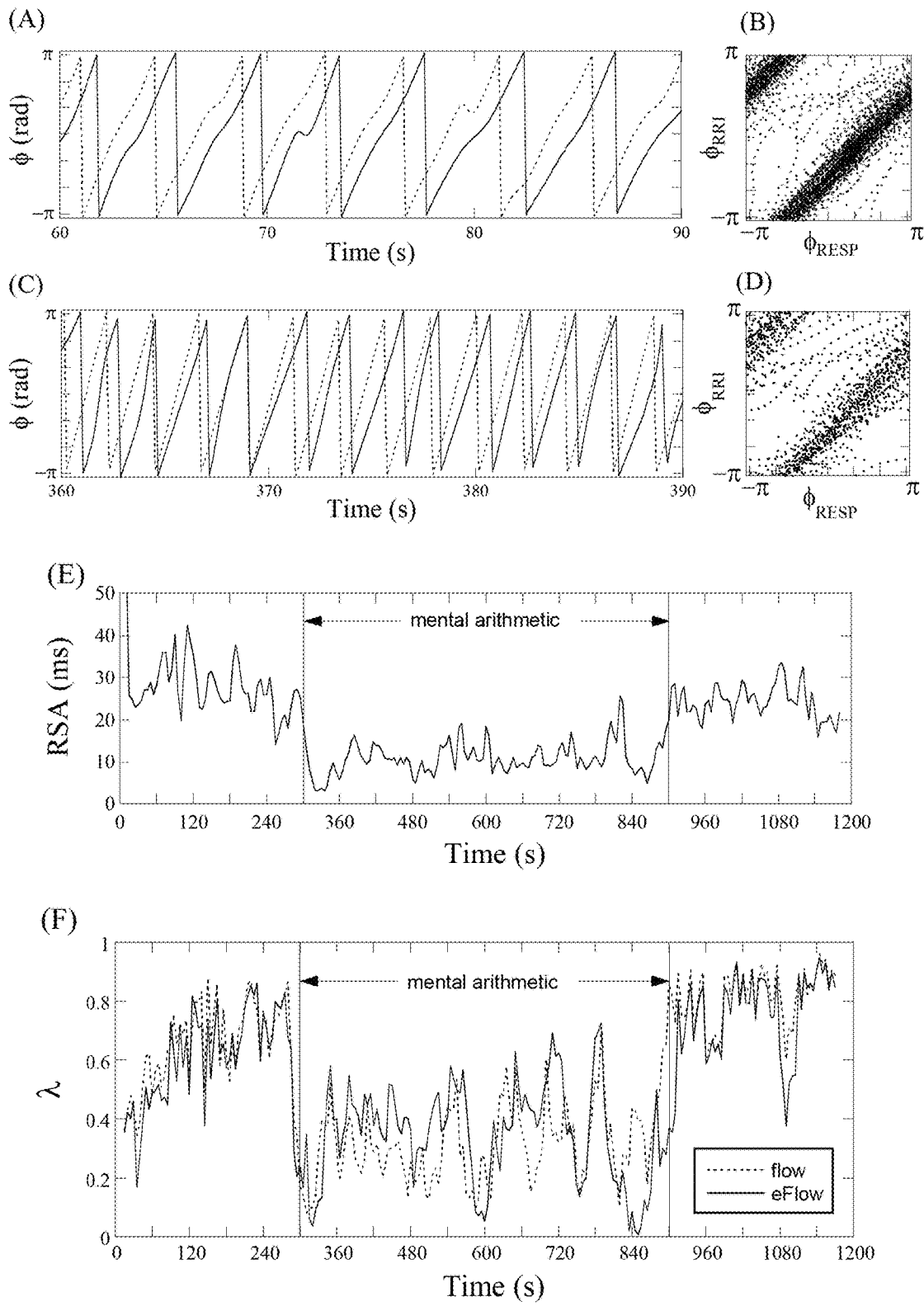
FIG. 10 (A) shows instantaneous phases of heartbeat (solid line) and breathing (dotted line) at rest; and (B) shows a Lissajous figure of instantaneous phases of heartbeat and breathing at rest. (C) shows instantaneous phases of heartbeat (solid line) and breathing (dotted line) during mental arithmetic (stress state); (D) shows a Lissajous figure of instantaneous phases of heartbeat and breathing during mental arithmetic; and (E) and (F) show changes in respiratory sinus arrhythmia (RSA) and phase coherence at rest and during mental arithmetic.

FIG. 10 shows instantaneous phase relationships between fluctuations in heartbeat interval and breathing pattern at rest and during mental arithmetic (stress state). FIG. 10 (A) shows instantaneous phases of heartbeat (solid line) and breathing (dotted line) at rest; and (B) shows a Lissajous figure of instantaneous phases of heartbeat and breathing at rest. FIG. 10 (C) shows instantaneous phases of heartbeat (solid line) and breathing (dotted line) during mental arithmetic (stress state); and (D) shows a Lissajous figure of instantaneous phases of heartbeat and breathing during mental arithmetic. FIG. 10 (E) shows changes in respiratory sinus arrhythmia (RSA) from rest state to mental arithmetic task and after end of the mental arithmetic task. FIG. 10 (F) shows changes in phase coherence from rest state to mental arithmetic task and after end of the mental arithmetic task; the dotted line represents phase coherence calculated using measured breathing pattern based on breathing airflow rate; and the solid line represents phase coherence calculated using breathing pattern calculated from electrocardiogram. The phase coherence is 0.69±0.12 (95% confidence interval, 0.63-0.75) at rest and 0.45±0.17 (95% confidence interval, 0.41-0.49) during mental arithmetic. The phase coherence is significantly lower during mental arithmetic than at rest. FIG. 10 indicates that instantaneous phase difference is adequately stable at rest, but mental stress such as mental arithmetic not only reduces size of respiratory sinus arrhythmia (RSA) but also disturbs phase difference. This means that stress upsets coordination between respiratory oscillator generated by the respiratory center and respiratory oscillator controlled by autonomic nervous system.

Figure 11:
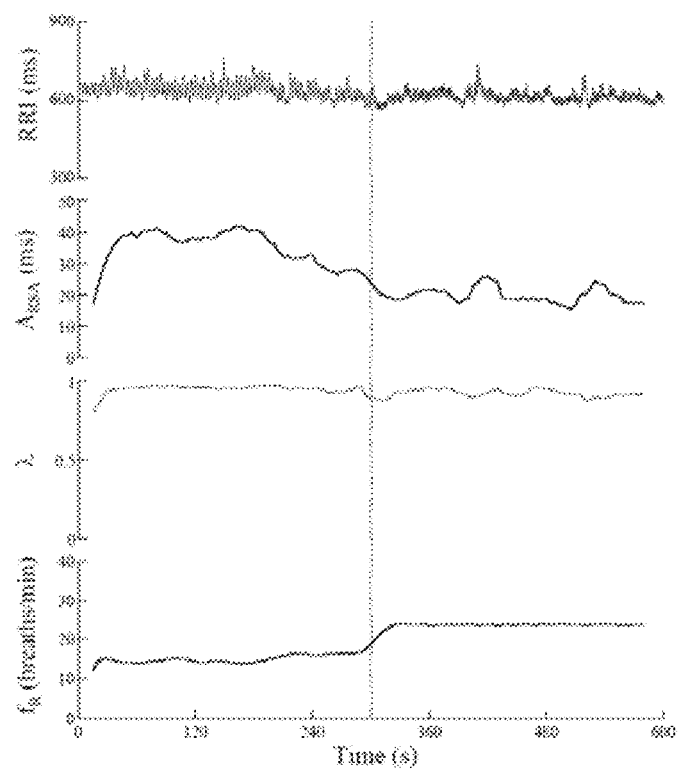
FIG. 11 The figure shows heart rate interval (R-R-interval, RRI), amplitude of respiratory sinus arrhythmia (ARSA), phase coherence (λ), and breathing frequency (FR) when the breathing frequency is voluntarily changed from 15/min to 25/min.

FIG. 11 shows heart rate interval (RRI), amplitude of respiratory sinus arrhythmia (ARSA), phase coherence ($\lambda$), and breathing frequency (FR) when the breathing frequency is voluntarily changed. Initially, the breathing rate was 15/min, but at 300 seconds, increased to 25/min voluntarily. The amplitude of respiratory sinus arrhythmia (ARSA) decreased with the increasing breathing rate, but the phase coherence almost remained unchanged. The respiratory sinus arrhythmia is a physiological event derived from parasympathetic neural activity in the autonomic nervous system, and its amplitude is said to correspond to the tense level of the parasympathetic neural activity. As shown in FIG. 11, the amplitude of respiratory sinus arrhythmia is affected even by the change of breathing rate, besides a change of the tense level, resulting in a failure to estimate autonomic activity from respiratory sinus arrhythmia. On the other hand, the phase coherence remains unchanged by the change of breathing rate, and thus autonomic activity can be accurately estimated from the phase coherence. Accordingly, measurement of phase coherence can facilitate examination of the mental stress state and sleep state of a subject in real-time independent of breathing frequency. Furthermore, size of respiratory sinus arrhythmia in a subject can be measured as an auxiliary assessment indicator of sleep state. Because fluctuations in heartbeat interval can be acquired as information, temporal changes in fluctuations in heartbeat interval are subjected to frequency analysis (Fourier transformation) to determine slow fluctuations component (low frequency, LF) and fast fluctuations component (high frequency, HF); and the ratio of LF to HF (LH/HF) and HF can be detected as a sympathetic neural activity indicator and a parasympathetic neural activity indicator, respectively. For example, temporal changes in fluctuations in heartbeat interval are subjected to Fourier transformation to obtain the power spectrum in which a component at 0.04 to 0.15 Hz and the other at 0.15 to 0.4 Hz may be calculated as LF and HF, respectively. These indicators are conventionally applied to analysis on fluctuations in heartbeat interval with respect to R waves obtained in electrocardiogram, but this invention accommodates use of fluctuations in heartbeat interval obtained from ballistocardiogram wave forms or bio-vibration signal in the analysis besides electrocardiogram, thereby allowing examination of accommodation disorder for sympathetic or parasympathetic neural activity. In addition, these indicators may be detected at the same time with the sleep state measuring device in this invention if electrocardiogram is used.

The desirable signal processing method on biological information containing information about heartbeat or containing information about breathing of a subject includes the filtering with cutoff frequency determined as the upper limit frequency or lower limit frequency from power spectrum of signals derived from the biological information. Determination of the upper limit frequency or lower limit frequency from power spectrum of signals derived from the biological information allows establishment of the filter that not only corresponds to biological information specific to the body of a subject and conditions at the time of acquisition such as posture, physical condition, and environment but also accommodates individual differences and conditions at the time of acquisition. Furthermore, it is desirable to renew the upper limit frequency or lower limit frequency of the filtering at regular or irregular interval basis, because the posture, physical condition, and environment always change.

Biological information containing information about heartbeat may be acquired, for example, from electrocardiogram, ballistocardiogram wave forms, and bio-vibration signals from measurement on temporal changes of vibrations (including ballistocardioaction) of a subject; and biological information containing information about breathing may be acquired, for example, from measured values on air flow caused by breathing, ones on changes in thoracic mechanical impedance associated with breathing, ones on changes in temperature caused by breathing, ones on abdomen movement associated with breathing movement, electrocardiogram, ballistocardiogram wave forms, and bio-vibration signals. Signals derived from biological information include not only biological information containing information about heartbeat or containing information about breathing as listed above but also pre-processed biological information thereof (information obtained after noise removal or accentuation processing). The concerned signal processing method may be applied to the following processing: for example, fluctuations in heartbeat interval is calculated from biological information containing heartbeat through a heart rate interval calculation function, or breathing pattern is calculated from biological information containing breathing pattern through a breathing pattern calculation function in the above sleep state measuring device; and fluctuations in heartbeat interval or breathing pattern is calculated from biological information containing both information about heartbeat and information about breathing of a subject in the phase coherence calculation device.

[Bio-Vibration Signal Measuring Device (Wearable Sensor)]

Figure 12:
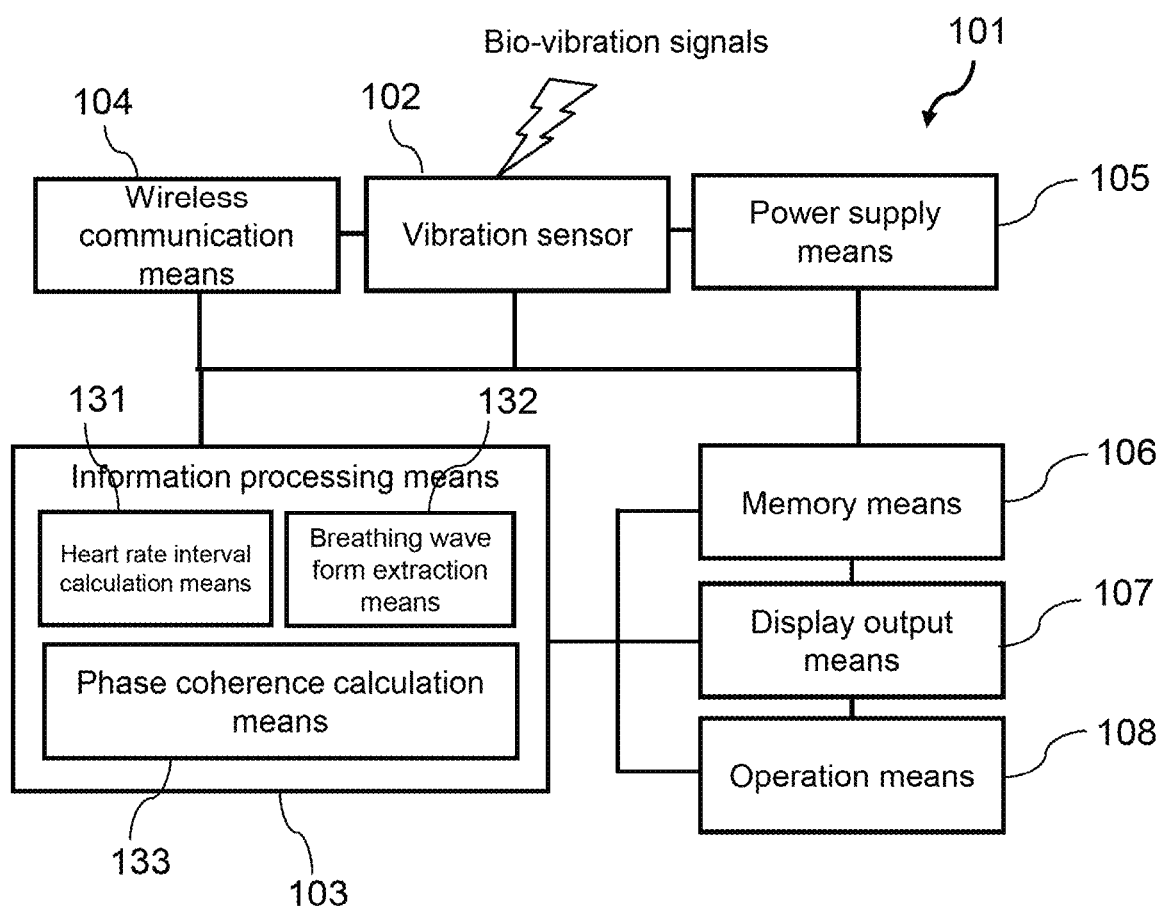
FIG. 12 The figure shows an overview block diagram of the bio-vibration signal measuring device in this invention.

FIG. 12 shows overview block diagram of the bio-vibration signal measuring device 101 in this invention. The bio-vibration signal measuring device 101 is provided with at least vibration sensor 102 in its wearing part that puts on a subject; and where necessary, it may be additionally provided with one or more of the information processing means 103, communication means 104, power supply means 105, memory means 106, display output means 107, and operation means 108. The wearing part is desirably a wearable one that can put on the body of a subject, for example, a limb or head of the subject. Of the upper limb of a subject, the finger, wrist, and arm are desirable body parts for attachment. For example, the sensor can be implemented on a ring, bracelet, fingerstall, wristband, etc. Of the lower limb of a subject, the thigh, shin, and ankle are desirable body parts for attachment. For example, the sensor may be implemented on a band, sock, spats, etc. Of the head of a subject, the neck, temple, and ear are desirable body parts for attachment. For example, the sensor may be implemented on a head band, necktie, necklace, pierced earring, etc.

The vibration sensor 102 is a sensor that measures vibrations, acquires bio-vibration signals containing information about heartbeat and information about breathing, and is wearable on a subject through the wearing part. FIG. 12 presents one vibration sensor 102, but multiple vibration sensors may be included, and where necessary, the other type of sensors (for example, optical sensor, temperature sensor) may be used in combination with the vibration sensor 102. If the vibration sensor 102 measures bio-vibration signals, the sampling frequency is desirably not less than 100 Hz. The vibration sensor 102 can be placed in direct or indirect contact with a subject to detect bio-vibration signals (may include ballistocardiogram wave forms). For the vibration sensor 102, a piezoelectric element or polymer piezoelectric element can be used. Bio-vibration signals detected with the vibration sensor 102 are transmitted to the information processing means 103, etc. through bus circuit in the device or the communication means 104.

The information processing means 103 is a means that processes input bio-vibration signals. For example, an electronic circuit or processing function of a central processing unit (CPU) may be used for the processing. The information processing means 103 is desirably placed in the bio-vibration signal measuring device 101, but apart from the bio-vibration signal measuring device 101, bio-vibration signals may be designed to be transmitted from the bio-vibration signal measuring device 101 through the communication means 104. Based on the processing function of CPU, frequency filtering can be achieved, for example, with digital filter. In addition, the information processing means 103 can be achieved with an analog circuit as well, but not a digital circuit. For example, frequency filtering may be achieved with an analog filter such as low-pass filter (LPF) and high-pass filter (HPF) consisting of condenser, resistance, and operational amplifier. The input bio-vibration signals in an analog format, where applicable, may be converted into digital signals through analog-digital conversion circuit.

The information processing means 103 includes at least the heart rate interval calculation means 131 and breathing wave form extraction means 132, and desirably the phase coherence calculation means 133. In addition, a device with a phase coherence calculation function may be called a "phase coherence calculation device." The bio-vibration signal measuring device 101 in this invention can be classified as a phase coherence calculation device, if it is provided with a phase coherence calculation function. Detailed processing procedures in the heart rate interval calculation means 131, breathing wave form extraction means 132, and phase coherence calculation means 133 are as explained for the above sleep state measuring device 1 and phase coherence calculation device 11.

The communication means 104 has a function to receive and transmit various signals through wired or wireless communication. The communication means 104 may be wire or cable connected to the vibration sensor 102. The wireless communication means 104 may send, for example, bio-vibration signals acquired with the vibration sensor 102 to the information processing means 103, memory means 106, display output means 107, and external devices (not shown in the figure), send information about phase coherence calculated with the information processing means 103 to the memory means 106, display output means 107, and external devices (not shown in the figure), or send bio-vibration signals or phase coherence stored in the memory means 106 to the information processing means 103 and display output means 107. The communication means 104 may send information input by user through the operation means 108 to the information processing means 103, memory means 106, and display output means 107. For the wireless communication means 104, for example, Bluetooth (trademark), Wi-Fi (trademark), or near field radio communication (NFC) is desirable. In addition, the communication means 104 does not necessarily have a two-way communication function depending on the modality of the bio-vibration signal measuring device 101.

The power supply means 105 has a function to supply power to each part of the bio-vibration signal measuring device 101. For example, battery such as lithium ion battery may be employed. The memory means 106 has a function to store bio-vibration signals acquired with the vibration sensor 102, processing results (such as phase coherence) calculated with the information processing means 103, and programs for operation of the information processing means 103. For example, memory may be employed.

The display output means 107 has a function to display or output calculation results such as phase coherence), various information input by the user, and details of the operation. For the display output means 107, a display that shows calculation results in image, a printer that outputs calculation results in paper, or a speaker that outputs calculation results in voice may be employed. The bio-vibration signal measuring device 101 may be provided with a display, which is used as the display output means 107.

The operation means 108 consists of a switch, touch panel, button, knob, keyboard, mouse, and voice input microphone to operate the bio-vibration signal measuring device 101. If the display output means 107 consists of a touch panel that can response to user's operations, the operation means 108 may be designed to serve as the display output means 107, too.

[Signal Processing Method]

In the bio-vibration signal measuring device 101, the information processing means 103 processes bio-vibration signals containing both information about heartbeat and information about breathing of a subject to acquire biological information. Biological information processed by the means include heart rate, heart rate interval, fluctuations in heartbeat interval (amplitude of respiratory sinus arrhythmia), breathing pattern, phase coherence, and frequency component of fluctuations in heartbeat interval.

For the phase coherence, instantaneous phase difference between fluctuations in heartbeat interval and breathing pattern in the same time series can be calculated from information about each heart rate interval and breathing pattern according to Equation (1) or (4) above.

Bio-vibration signals acquired with the vibration sensor 102 are input into an analog-digital conversion circuit, which is not included in the figure of the information processing means 103. The analog-digital conversion circuit is a circuit that converts analog signals from the vibration sensor 102 into digital signals. If the vibration sensor 102 is provided with the analog-digital conversion circuit, or if the vibration sensor 102 is designed to detect digital signals, the information processing means 103 may not be provided with the analog-digital conversion circuit. In addition, analog signals that have been acquired with the vibration sensor 102 and then filtered may be converted into digital signals by the analog-digital conversion circuit.

The bio-vibration signals converted into a digital form are input into the heart rate interval calculation means 131 and breathing wave form extraction means 132 of the information processing means 103. As a means prior to the heart rate interval calculation means 131, a heartbeat extraction means, which is not included in the figure, may be placed. In the information processing means 103, for example, analog signal acquired with the vibration sensor 102, when input, are subjected to an analog filter such as low-pass filter (LPF) and high-pass filter (HPF), and filtered signals are then amplified with an operational amplifier. In addition, it may be provided with an automatic gain control circuit (AGC circuit) which is capable of automatically controlling individually different signal levels. This circuit may be performed as follows: for example, whether signals amplified with the operational amplifier fall within a proper range is assessed, and then feedback of the concerned assessment information is made to facilitate determination of the amplification efficiency.

The heartbeat extraction means, which is not included in the figure, is a means that extracts information about heartbeat from bio-vibration signals detected with the vibration sensor 102, and appropriate processing is selected based on input bio-vibration signals. Because bio-vibration signals (containing ballistocardiogram wave forms) usually contain not only vibrations based on ballistocardioaction caused by heart beating, but also vibrations caused by breathing, body movements, vocalization, and external environment, it is desirable to perform processing to remove these noises. If heart rate interval is calculated without any problem, the heartbeat extraction means may not be used. The processing to remove the concerned noises may be performed by the above method: for example, strength of the bio-vibration signals is raised to the Nth power for accentuation processing followed by band-pass filtering (BPF). Furthermore, a method to calculate heart rate interval from the above ballistocardiogram wave forms may be used as one to calculated heart rate interval from bio-vibration signals.

In addition, to determine further accurate heartbeat from bio-vibration signals, the following calculation may be performed: transfer characteristic of ballistocardioaction is calculated to estimate inverse transfer function, by which wave forms equivalent to electrocardiogram are determined from bio-vibration signals. For the inverse transfer function, transfer characteristic may be investigated by prior measurement of electrocardiogram and ballistocardiogram of a subject, but it can be estimated only from bio-vibration signals.

The information about heartbeat extracted by the heartbeat extraction means are input into the heart rate interval calculation means 131. The heart rate interval calculation means 131 calculates heart rate interval from information about heartbeat. To measure heartbeat interval using electrocardiogram, an interval from an R wave to the next R wave is desirably measured, because R waves have a sharp peak. Even when information about heartbeat extracted from bio-vibration signals are used, an interval of wave forms corresponding to R waves with sharp peak is desirably measured as with the above.

The breathing wave form extraction means 132 extracts breathing pattern from bio-vibration signals containing both information about heartbeat and information about breathing detected with the vibration sensor 102. For the breathing wave form extraction means 132, appropriate processing is selected based on input bio-vibration signals. The breathing wave form extraction means 132 may perform processing to remove noise signals. When signals related to breathing pattern are extracted from bio-vibration signals, the following processing may be performed: for example, strength of the bio-vibration signals is raised to the Nth power (N is an integer not less than 2, and if N is odd, the absolute value is used) for accentuation processing followed by low-pass filtering (LPF) with the pass band of the frequency not more than 0.5 Hz. The LPF cutoff frequency of the breathing wave form extraction means 132 may be 0.3, 0.4, 0.6, 0.7, or 0.8 Hz. In addition, the cutoff frequency of the breathing wave form extraction means 132 may be the same as the lower limit frequency of the heartbeat extraction means or higher than the lower limit frequency, even which results in superimposition of a part of the pass band. For the breathing wave form extraction method, it is desirable to determine the upper limit frequency or lower limit frequency of the filtering based on the acquired bio-vibration signals. Furthermore, it is more desirable to determine the upper limit frequency or lower limit frequency of the filtering based on the acquired bio-vibration signals at regular or irregular intervals. The cutoff frequency may be determined as follows: firstly, power spectrum is determined from bio-vibration signals or pre-processed signals thereof (signals obtained after filtering for noise removal or accentuation processing); the initial peak is identified by scanning the power spectral density starting from low frequency side; and the frequency on the high frequency side where the peak signal is decreased to a specified threshold (for example, half-width height) may be used as cutoff frequency. Signal processing using the filtering with the upper limit frequency or lower limit frequency determined from the acquired bio-vibration signal, as the above, achieved establishment of the filter that not only corresponds to biological information specific to a subject and conditions at the time of acquisition such as posture, physical condition, and environment but also accommodates individual differences and conditions at the time of acquisition. Thereby, phase coherence has been calculated in real time. In addition, BPF may be used for filtering in place of LPF. In this case, the lower limit frequency of BPF is only required to be sufficiently low; for example, it may be set at 0.1 Hz.

The heart rate interval calculated by the heart rate interval calculation means 131 and breathing pattern extracted by the breathing wave form extraction means 132 are input into the phase coherence calculation means 133. The phase coherence calculation means 133 has an instantaneous phase calculation function (Hilbert transformation filter) to calculate instantaneous phase of fluctuations in heartbeat interval and that of breathing pattern; an instantaneous phase difference calculation function (instantaneous phase difference calculation means) to calculate instantaneous phase difference between the above instantaneous phases; and a phase coherence calculation function to calculate phase coherence from the calculated instantaneous phase difference. The Hilbert transformation filter not included in the figure outputs instantaneous phases and instantaneous amplitudes of fluctuations in heartbeat interval and breathing pattern. As a Hilbert transformation filter, the same filter as the Hilbert transformation filter 35 or 36 in the sleep state measuring device 1 presented in FIG. 3 can be employed.

The instantaneous phase difference calculation means, which is not included in the figure, calculates phase difference (instantaneous phase difference) between instantaneous phase of fluctuations in heartbeat interval and instantaneous phase of breathing pattern, and outputs the results to the phase coherence calculation means 133. Then, the phase coherence calculation means 133 calculates phase coherence using the instantaneous phase difference between fluctuations in heartbeat interval and breathing pattern. Data used to determine the phase coherence shall be obtained by calculation with a window size of at least 1 breathing cycle.

To acquire bio-vibration signals, the vibration sensor 102 may be placed in direct contact with a subject or in indirect contact with a subject through a wearing part made from a component to which vibrations are transmitted (for example, ring, bracelet, and belt). More specifically, a wearing part desirably contains materials for thin-film ceramics such as PZT, BST, PN, and PT, ferroelectric substances, or materials for organic thin-film such as PVDF. Both sides of such thin-film are coated with electrode substances. Applicable electrode substances are metals such as Pt/Ti, Au, Al, and Cu. That is, sandwich structure in which metal substances cover both sides of a ferroelectric material (thin-film?) as electrodes is formed. To one side of this electrode component, a plastic or rubber material, which can transmit vibrations, is applied or affixed so that the component will have a function to detect vibrations caused by blood flow. Measurement of blood flow in the finger may be achieved using an anatomical characteristic of the finger in which blood vessels run on both side as follows: the sandwich structure component is wrapped around the finger with an elastic material to detect blood flow movements as vibration signals that occur around the finger. Desirable elastic materials are rubber materials and elastic plastic materials. Or metals such as Au, Ag, and Pt, which are used as materials of a ring, may be used although these are less elastic. These metals can be used as materials that transmit vibrations caused by blood flow. The vibration sensor 102 as described above can be in an extremely thin sheet form and thus have free flat area. Furthermore, because the sensor is thin and flexible, it can be wrapped or affixed around a column component or a part of the body, taking advantage of these characteristics. For such application, the sensor may be made of a thin (10-200 μm in thickness) organic film sheet or a coated organic film sheet in which a piezoelectric material such as PVDF is coated <10 μm in thickness on the base organic film such as PEN and PET. Such thin and flexible sensor can be versatile at applications.

After acquisition of bio-vibration signals, information about heartbeat and information about breathing have to be extracted separately. The information about heartbeat and information about breathing can be extracted according to frequency using low-pass filter (LPF), band-pass filter (BPF), and high-pass filter (HPF).

The desirable signal processing method on bio-vibration signals containing information about heartbeat and information about breathing of a subject includes the filtering with cutoff frequency determined as the upper limit frequency or lower limit frequency from power spectrum of signals derived from bio-vibration signals. Determination of the upper limit frequency or lower limit frequency from power spectrum of signals derived from the bio-vibration signals allows establishment of the filter that not only corresponds to biological information specific to the subject and conditions at the time of acquisition such as posture, physical condition, and environment but also accommodates individual differences and conditions at the time of acquisition. Furthermore, it is desirable to renew the upper limit frequency or lower limit frequency of the filtering at regular or irregular interval basis, because the posture, physical condition, and environment always change.

In this this invention, bio-vibration signals from measurement on temporal changes of vibrations (including ballistocardioaction) are available as biological information containing information about heartbeat and information about breathing. Not only bio-vibration signals themselves but also pre-processed signals thereof (for example, signals after noise removal or accentuation processing) are available. The concerned signal processing method may be applied to calculation of fluctuations in heartbeat interval or breathing pattern from bio-vibration signals containing both information about heartbeat and information about breathing of a subject.

Furthermore, the information processing part 103 may have an assessment function to assess sleep state based on calculated phase coherence. In the assessment function, for example, if the calculated phase coherence is larger than the threshold, the sleep state may be assessed as a deep state; or if it is smaller than the threshold, the sleep state may be assessed as a shallow state; the sleep quality may be evaluated based on the duration in which the phase coherence remains higher than the threshold; or the sleep quality may be evaluated based on the cycle of fluctuations of the phase coherence. The threshold may be a predetermined value, be specified based on previously calculated phase coherence values in the measurement subject, or be set at multiple levels for step-wise evaluation of the sleep quality. Furthermore, the information processing part 103 can assess breathing state during sleep with the assessment function. For example, depending on the breathing pattern acquisition method, but with any acquisition method, for central sleep apnea (apnea resulted from discontinuation of breathing movement due to abnormality in the respiratory center in the brain), non-breathing state can be found based on a failure of detection of the breathing pattern due to discontinuation of the breathing movement.

In this example, biological information were acquired using a sheet-type piezoelectric sensor (piezoelectric element) as a sensor for measurement of vibrations, and from the concerned biological information, phase coherence was determined. At the same time, breathing pattern of a subject is measured using electrocardiogram and hot-wire breathing flowmeter, and from the above biological information, phase coherence was determined.

Figure 13:
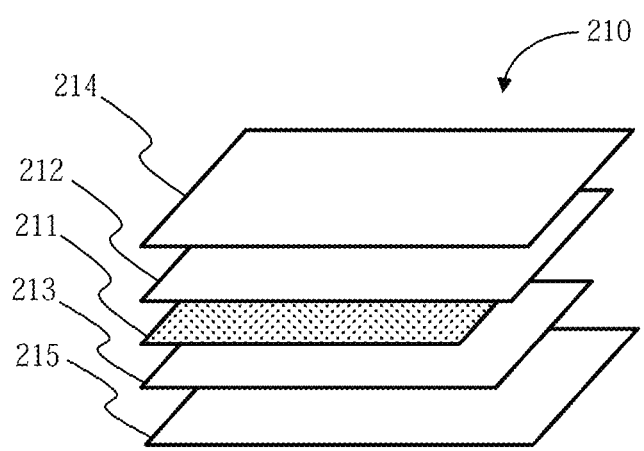
FIG. 13 The figure shows a configuration of a sheet-type piezoelectric sensor.

FIG. 13 shows a structure of the sheet-type piezoelectric sensor 210 used in this example. The structure of the sheet-type piezoelectric sensor 210 is as follows: the top and under surfaces of the sheet-type vibration sensor material 211 are covered with the positive electrode layer 212 and negative electrode layer 213, respectively, which are furthermore protected with the outer covers 214 and 215. As the vibration sensor material 211, polyvinylidene difluoride (PVDF), a fluoride organic thin film ferroelectric material, was used. In addition, signals may be retrieved from the top and under electrodes, but the potential of the negative electrode layer 213 can be kept constant so that signals generated by displacement of the vibration sensor material 211 can be retrieved from the positive electrode layer 212. The outer covers 214 and 215 may function as shielding layers with the constant potential kept to remove various external noise, especially, electromagnetic noise. Or, the shielding layer can be designed to have the same potential as that in the negative electrode layer 213. In this case, the negative electrode layer and the protective cover can be integrated into one component. In addition, an insulating layer (insulating sheet) may be placed between the positive electrode layer 212 or negative electrode layer 213 and the outer cover 214 or 215 to insulate these components. On the positive electrode layer 212 and negative electrode layer 213, retrieval terminals are implemented with filter circuits to enable voltage application to these electrodes or signal output from the electrodes. The piezoelectric sensor 210 is a piezoelectric element. When mechanical (minimal) force is applied, the vibration sensor material 211 generates electromotive force that can convert electrical charge accumulated in this material into current and voltage, allowing retrieval of electric signals.

In this example, the sheet-type piezoelectric sensor 210 was placed under a bed sheet to isolate and extract bio-signals from the subject in a stress-free state without restraint. For measurement on the bed, the sheet-type piezoelectric sensor 210 was placed between a sheet and the bed mattress, and a subject took a rest at the supine position. When a subject lies on the bed, movements of the heart and breathing are transmitted to the sensor 210 as vibration waves through the body and body surface, and then the sensor 210 generates electromotive force on the order of $\mu V$. Because such signals contained not only intended biological information about heartbeat and breathing but also interfering noise signals, the biological information about heartbeat and breathing were isolated and extracted subsequently using the signal processing algorithm (electronic circuit and software). In addition, the subject had an electrode for electrocardiogram affixed to the chest to measure the electrocardiogram (ECG) with a monopolar lead at the same time. Furthermore, the subject wore a face mask to measure the breathing pattern at the same time with a hot-wire breathing flowmeter. In addition, when the sheet-type piezoelectric sensor 210 was placed under the thin cushion on the seat of a chair, bio-signals were also successfully detected from a subject sitting on the chair.

Bio-vibration signals as well as electrocardiogram and breathing airflow rate wave forms were sampled at 100 Hz and saved. Bio-vibration signals were processed using specified digital filters for detection of heartbeat and breathing as follows: Bio-vibration signals were passed through high frequency band-pass filter (or high-pass filter) followed by full-wave rectification integration to extract heartbeat-derived vibration component only; for determination of peaks of the above wave forms, the extracted heartbeat-derived vibration component wave forms were differentiated; by setting the threshold, peaks (heartbeat pulse) were detected; and from intervals between the peaks, beating intervals were determined. In this section, heart rate interval determined from the electrocardiogram and one from the bio-vibration signals are referred to as RRI and BBI, respectively. In addition, bio-vibration signals were passed through low frequency band-pass filter (or low-pass filter) to extract breathing-derived vibration component, from which breathing pattern was estimated. RRI and BBI were re-sampled at 10 Hz by spline interpolation. Breathing pattern measured with the hot-wire breathing flowmeter and that estimated from the bio-vibration signals were also re-sampled at 10 Hz. Respiratory sinus arrhythmia and breathing pattern were subjected to Hilbert transformation; from the obtained analysis signals, instantaneous phases were determined; from their phase difference $\Psi$, phase coherence $\lambda$ was calculated. The phase coherence was determined by shifting a 10-second calculation window by 5 seconds at a time.

Figure 14:
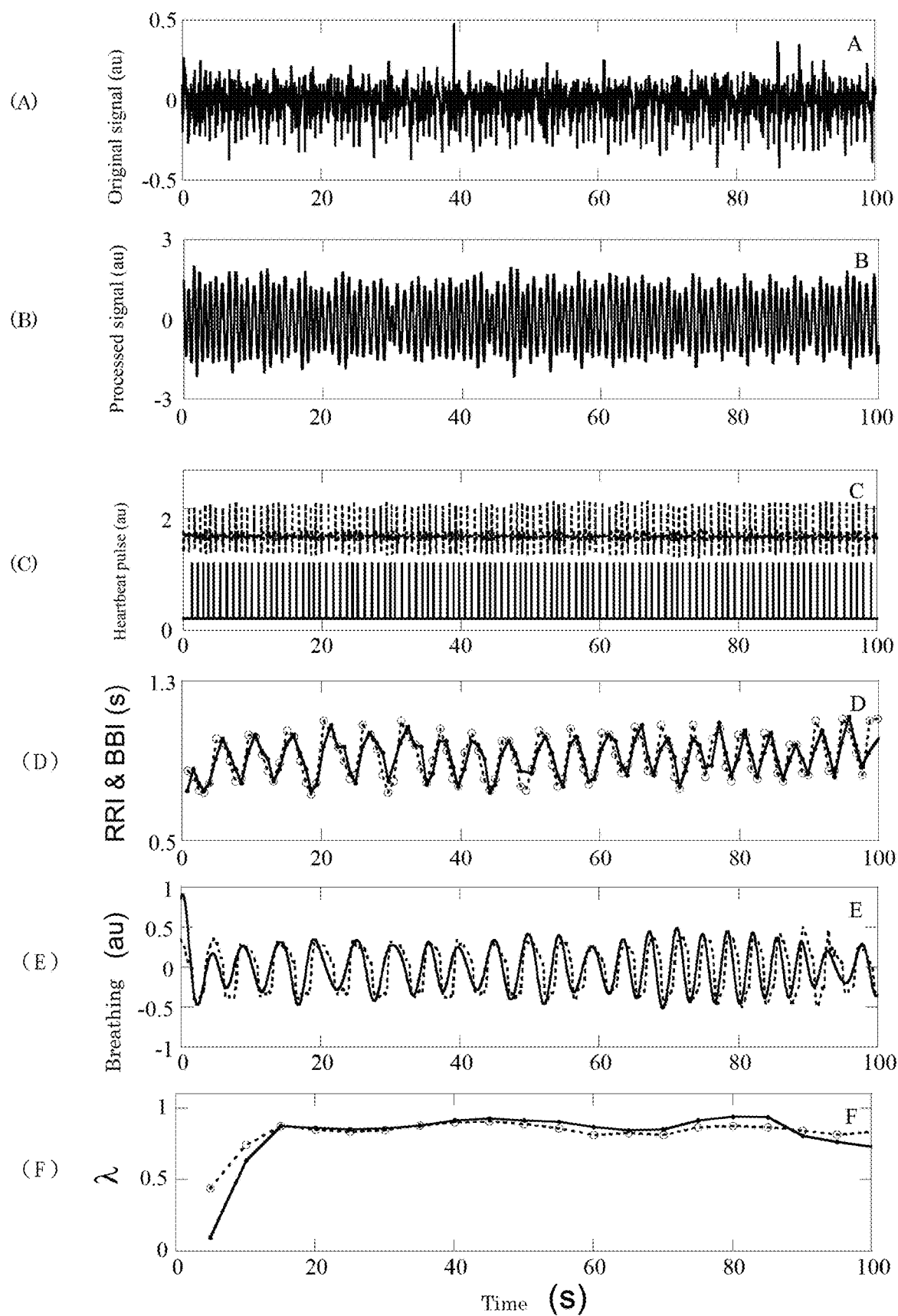
FIG. 14 The figure shows signal wave foils detected or calculated in test examples.

FIG. 14 (A) shows original bio-vibration signals acquired with the sheet-type piezoelectric sensor 210. FIG. 14 (B) shows wave forms obtained by processing of the original signals (after differentiation of heartbeat-derived vibration component wave forms obtained by the full-wave rectification integration). FIG. 14 (C) shows heartbeat pulse obtained from the electrocardiogram (dotted line) at the top and heartbeat pulse (solid line) obtained from the signal-processed wave forms at the bottom. FIG. 14 (D) shows RRI (dotted line) determined from the electrocardiogram and BBI (solid line) from the bio-vibration signals. FIG. 14 (E) shows measured breathing pattern (dotted line) and breathing pattern (solid line) estimated from the bio-vibration signals. FIG. 14 (F) shows phase coherence (dotted line) calculated from electrocardiogram and measured breathing pattern and phase coherence (solid line) estimated from the bio-vibration signals. As shown in FIG. 14 (D), RRI simultaneously obtained from the electrocardiogram is closely similar to BBI determined from the bio-vibration signals, demonstrating successful calculation of fluctuations in heartbeat interval from bio-vibration signals through signal processing. As shown in FIG. 14 (E), the measured breathing pattern also almost agrees with breathing pattern estimated from the bio-vibration signals. Furthermore, as shown in FIG. 14 (F), phase coherence calculated from electrocardiogram and measured breathing pattern almost agrees with that calculated from bio-vibration signals alone. As demonstrated above, only measurement of bio-vibration signals successfully allowed calculation of fluctuations in heartbeat interval (respiratory sinus arrhythmia), breathing pattern, and phase coherence.

Figure 15:
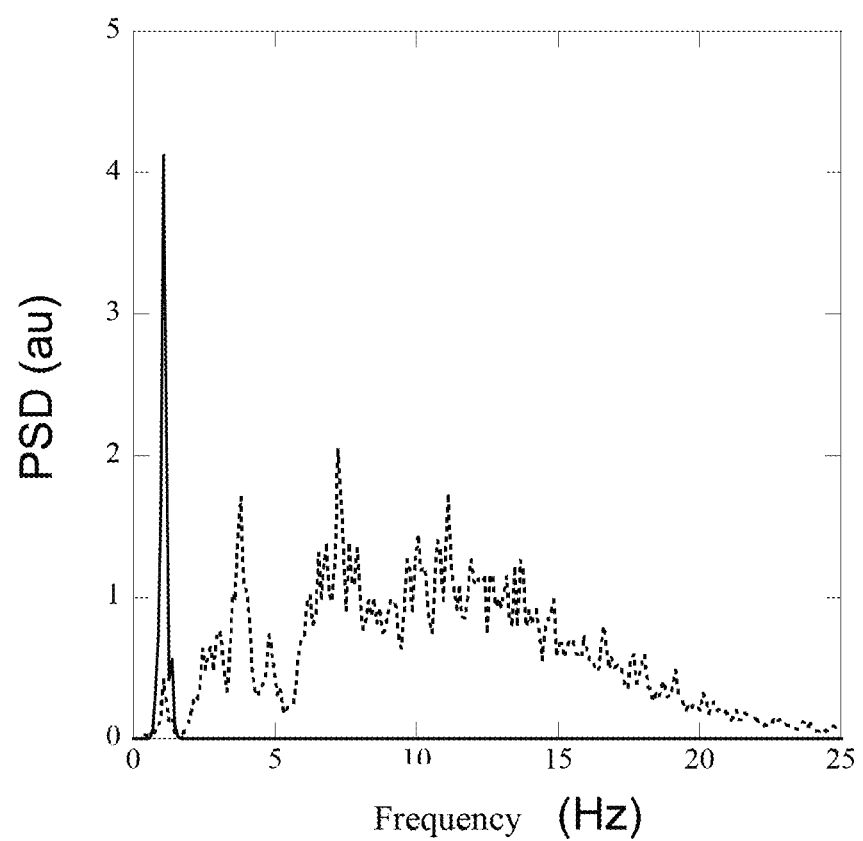
FIG. 15 The figure shows power spectral density (PSD) of signal derived from electrocardiogram and bio-vibration signal.

FIG. 15 shows power spectral density (dotted line) of the electrocardiogram and power spectral density (solid line) of wave forms obtained by processing of bio-vibration signals shown in FIG. 14 (B). Heartbeat frequency (approximately 1 Hz), fundamental frequency in the electrocardiogram, agrees with peaks in the power spectrum of wave forms obtained by signal processing, indicating that signal processing removed signals other than fundamental frequency component from the electrocardiogram to obtain the wave forms. As described above, when BBI corresponding to RRI is determined from heartbeat-derived vibration component after complete removal of the breathing frequency component, the BBI is accurate. The above determination has allowed detection of respiratory sinus arrhythmia corresponding to fluctuations in heartbeat interval and calculation of phase coherence that almost agrees with that determined from the electrocardiogram and measured breathing.

The phase coherence calculation device in this invention can be integrated in various pieces of furniture and electronic equipment. For example, a sensor for measurement of vibrations may be integrated in a chair or an article of bedclothes to measure stress state of a user. In this case, such idea can be applied to seats in trains and air planes, chairs at work places, driver's seat of cars, trains, and air planes for management of stress and prevention of a doze, or to beds in hospitals and nursing homes for management of heath conditions of patients. In addition, a sensor for measurement of vibrations may be integrated in the floor of a toilet room, bath room, and changing room for monitoring of events such as syncope and cerebral stroke. Furthermore, the phase coherence calculation device can be integrated in a portable terminal or computer for assessment of mental stress in various settings of daily life.

Example 2

Figure 16:
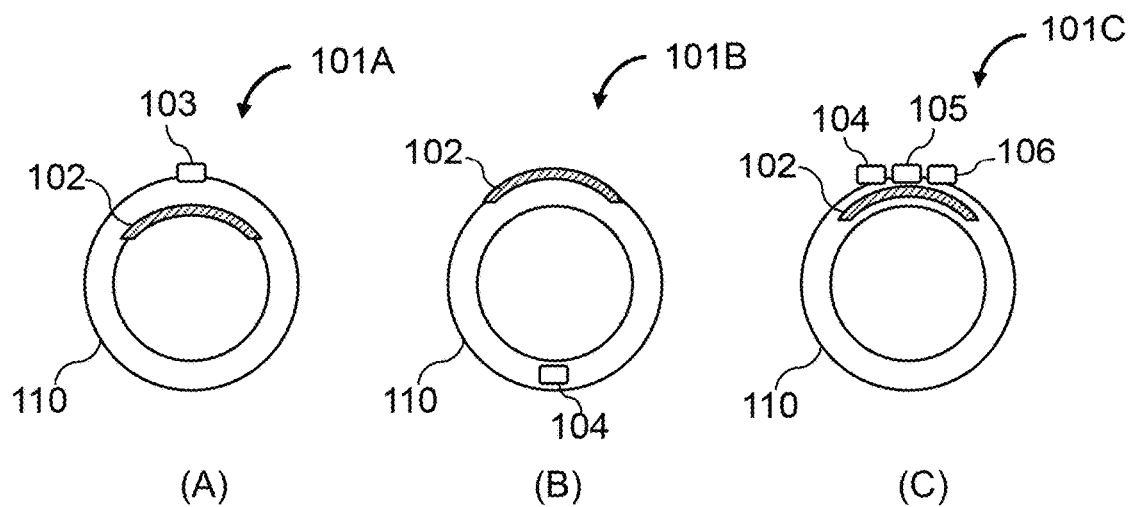
FIG. 16 shows an overview diagram of configuration of the ring-type bio-vibration signal measuring device in Operating form 1.

FIG. 16 shows an overview diagram of configuration of the ring-type bio-vibration signal measuring device. The ring-type bio-vibration signal measuring device is designed to be wearable on fingers of a subject and has a function to acquire bio-vibration signals of the finger containing both information about heartbeat and information about breathing. It may not have a function to calculate phase coherence from the bio-vibration signals of the finger. The bio-vibration signals of the finger are in a form of pulse wave (changes in blood pressure or volume in peripheral arteries associated with beating of the heart) and affected by ballistocardioaction.

As shown in FIGS. 16 (A), (B), and (C), the ring-type bio-vibration signal measuring device 101 (101A, 101B, 101C) include at least the vibration sensor 102 and may include information processing means 103, communication means 104, power supply means 105, and memory means 106 where necessary. The vibration sensor 102 may be implemented on the inside surface of the ring component 110 (wearing part) as shown in FIG. 16 (A) or on the outer surface of the ring component 110 as shown in FIG. 16 (B). Or, as shown in FIG. 16 (C), it may be implanted in the ring component 110. The vibration sensor 102 in FIG. 16 (A) comes in direct contact with the finger of a subject, allowing direct acquisition of bio-vibration signals of the finger. The vibration sensor 102 shown in FIG. 16 (B) and FIG. 16 (C) can indirectly acquire bio-vibration signals of the finger through the ring component 110. In this case, the ring component 110 is desirably made of materials that can readily transmit bio-vibration signals (for example, metal, rubber, resin, and leather). The vibration sensor 102 may have any configuration that allows detection of vibrations of the finger, but it is desirable to be a piezoelectric sensor (see FIG. 18) that is designed to be in direct or indirect contact with the finger.

In the example in FIG. 16 (A), the ring-type bio-vibration signal measuring device 101A includes vibration sensor 102 and information processing means 103. The information processing means 103 is a computation device, processes bio-vibration signals of the finger acquired with the vibration sensor 102, includes operational amplifier, feedback circuit, filter circuit, and comparator, and is designed to achieve functions of the heart rate interval calculation means, breathing wave form extraction means, and phase coherence calculation means The bio-vibration signal measuring device 101A in FIG. 16 (A) outputs bio-vibration signals acquired by the communication means or display means, not included in the figure, or calculated biological information. The ring-type bio-vibration signal measuring device 101A shown in FIG. 16 (A) is also classified as a phase coherence calculation device, because it has a phase coherence calculation function (information processing means 103). In the example in FIG. 16 (B), on the other hand, the bio-vibration signal measuring device 101B is not provided with the phase coherence calculation function (information processing means 103) and is designed as a bio-vibration signal acquisition device that simply acquires bio-vibration information of a subject. It thus sends the signals externally (for example, cellular phone, smart phone, personal computer) through the communication means 104 or displays the acquired bio-vibration signals on a display means, not included in the figure.

In the example in FIG. 16 (C), the bio-vibration signal measuring device 1010 is provided with the vibration sensor 102, communication means 104, power supply means 105, and memory means 106. The memory means 106 (for example, memory) stores bio-vibration signals acquired with the vibration sensor 102. The communication means 104 (for example, Bluetooth (trademark)) can send the bio-vibration signals to an information processing means in external devices (for example, cellular phone, smart phone, personal computer). The power supply means 105 (for example, battery) can supply electric power to the vibration sensor 102, information processing means 103, communication means 104, and memory means 106.

Each modality of the ring-type bio-vibration signal measuring device 101 in FIG. 16 is an example, and this invention is not limited to the above. For example, the bio-vibration signal measuring device 101A in FIG. 16 (A) may be designed to include the memory means 106 so that bio-vibration signals acquired with the vibration sensor 102 can be transiently stored in the memory means 106 and then output externally through a wired or wireless communication means. In addition, the bio-vibration signal measuring device 101B in FIG. 16(B) may be designed to include the memory means 106 so that bio-vibration signals acquired with the vibration sensor 102 can be transiently stored and then sent externally (for example, cellular phone, smart phone, personal computer) through a communication function.

If a vibration sensor is used to acquire bio-vibration signals, the ring-type bio-vibration signal measuring device is intended to measure expansion of the finger circumference caused by arterial blood flow in the finger. Therefore, it may be attached to tighten the finger to some extent, but the wearing site is not limited to the root, and the vibration sensor can be placed at any site independent of blood vessel distribution in the finger as long as it is in direct or indirect contact with the finger surface. In addition, a piezoelectric sensor generates electric signals in response to vibrations. If it is used, it can acquire bio-vibration signals without requiring electric power and convert them into electric signals, allowing operation with minimum power consumption. Therefore, it is suitable for long-term use. Furthermore, such piezoelectric sensor can facilitate development of a small and light-weight device, because it does not require implementation of a large-capacity battery.

For the ring-type bio-vibration signal measuring device 101, the information processing means 103 and communication means 104 are desirably stacked within a small partial area in the ring. These means may be directly stacked on the top of the vibration sensor 102. This would result in a structure in which the vibration sensor 102, information processing means including an analog part, and communication means 104 are stacked in a three-dimensional fashion. Furthermore, the power supply means 105 such as a lithium ion battery can be stacked.

A wearable device such as a ring-type, if configured, desirably has a system that does not consume electric power, and the long-life power supply means 105 (lithium ion battery) has an advantage. Therefore, the system desirably has the minimum required function; the information processing means 103 can be provided only with an analog circuit including an automatic gain control circuit (AGC circuit), AD conversion circuit, operational amplifier, and filter as well as a connection part linked to a communication means. In this case, the information processing part 103 implemented on the ring component desirably includes the heart rate interval calculation means 131 and breathing wave form extraction means 132 only with the other means such as the phase coherence calculation means 133 placed in external devices (smart phone, PC server, cloud system). Furthermore, the following processing flow may be possible: signals processed by the information processing part 103 implemented on the ring component are sent to an external device by the communication means 104, and then final information processing and information output are achieved by the external device.

Example 3

Figure 17:
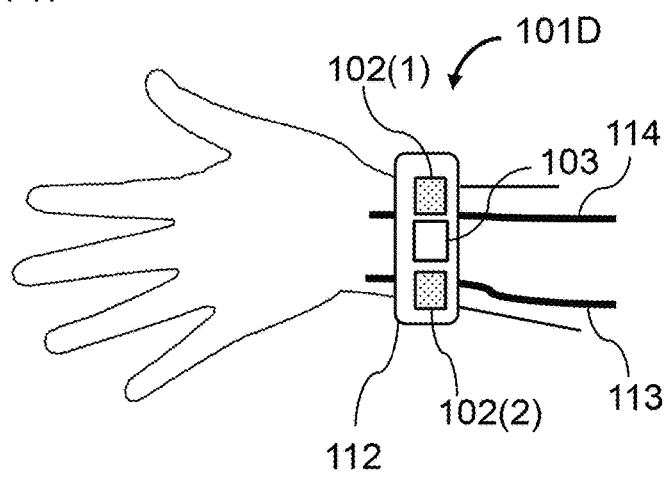

FIG. 17 shows an overview diagram of configuration of the bracelet-type bio-vibration signal measuring device. The bracelet-type bio-vibration signal measuring device 1D is designed to be wearable on the wrist of a subject (FIG. 17 illustrates the palm of the right hand) and consists of two vibration sensors 102 (102 (1), 102 (2)), the information processing means 103 connected to the two vibration sensors 102, and band 112 (wearing part) housing the vibration sensor 102 and information processing means 103.

As shown in FIG. 17, in the wrist of a human, the ulnar artery 113 and radial artery 114 run on the little finger side and thumb side, respectively. The vibration sensor 102 (1) is placed above the ulnar artery 113 and the other sensor 102 (2) is above the radial artery 114. The bracelet-type bio-vibration signal measuring device 101D, therefore, can acquire bio-vibration signals of the wrist from these two arteries.

Although the bracelet-type bio-vibration signal measuring device 101D in FIG. 17 is configured to include the information processing means 103, but the device is not limited to this configuration. A memory means that stores bio-vibration signals acquired with the vibration sensor 102 may be included to send the signals to an external information processing means through an appropriate communication means (for example, Bluetooth (trademark)), or a display means may be included to display the bio-vibration signals or biological information. Although two vibration sensors 102 are presented in FIG. 17, it is an example, and this invention is not limited to the above. The vibration sensors 102 are designed to form a long strap. The concerned vibration sensors 102 may be attached to wrap the whole or a part of the circumference of the wrist, or only either sensor may be used. In addition, if the information processing means 103 is included in a bracelet-type bio-vibration signal measuring device, it may be designed to send signal processing results to an external device (for example, portable terminal, computer) through an appropriate communication means. The signal processing results may be displayed on an external display device. A piezoelectric sensor is desirably used as the vibration sensor 102 (hereinafter referred to as the piezoelectric sensor 102 occasionally).

A bracelet-type bio-vibration signal measuring device measures bio-vibration signals of the wrist at two sites, allowing calculation of heart rate interval, respiratory sinus arrhythmia, and phase coherence from two sets of bio-signals and thereby improving assessment of the sleep state or stress state in precision. For a vibration sensor, if used, the wrist has to be tightened at a certain strength, which may cause discomfort in a subject. In addition, if it is not closely adhered to the skin due to inadequate tightening, generating a gap between the vibration sensor and wrist surface can obscure the acquired bio-vibration signals. Furthermore, the vibration sensor has to be placed above at least either the ulnar artery 113 or radial artery 114. Otherwise, it would be difficult to measure vibrations accurately. Arrangement of the vibration sensors 102 is restricted. In this aspect, the ring-type bio-vibration signal measuring device is more appropriate for implementation of a piezoelectric sensor. Even if the finger circumference is tightened at a certain strength, discomfort is unlikely to occur in a subject, and noise is also unlikely to be generated.

Figure 18:
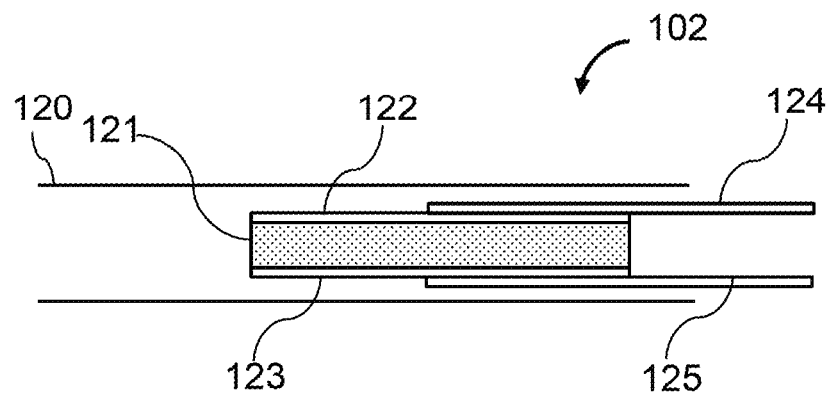
FIG. 18 The figure shows an example of the vibration sensor (piezoelectric sensor).

FIG. 18 shows a cross section of the sheet in the examples of the vibration sensor 102 in FIG. 12, FIG. 16, and FIG. 17. The structure of the vibration sensor 102 is as follows: the top and under surfaces of the sheet-type vibration sensor material 121 is covered with the signal electrode layer 122 and earth electrode layer 123, which are then connected with the top feeder electrode 124 and under feeder electrode 125, respectively. The vibration sensor 102 is at least partially protected with the cover 120. As the vibration sensor material 121, polyvinylidene difluoride (PVDF), a fluoride organic thin film ferroelectric material, can be used. The piezoelectric sensor 102 may be a piezoelectric element. In this case, when mechanical (minimal) force is applied, the vibration sensor material 121 generates electromotive force that can convert electrical charge accumulated in this material into current and voltage, allowing retrieval of electric signals.

If the ring component 110 shown in FIG. 16 is made of an electric conductive material, the top feeder electrode 124 and under feeder electrode 125 in the piezoelectric sensor 102 may be connected with the ring component 110 so that bio-vibration signals acquired with the piezoelectric sensor 102 are input in the information processing means 103 through the ring component 110. In addition, the top feeder electrode 124 and under feeder electrode 125 may be connected with an input terminal such as the information processing means 103, communication means 104, and memory means 106 shown in FIG. 16 or FIG. 17.

Example 4

In this example, the ring-type bio-vibration signal measuring device was attached to the root and thick of the index finger as well as the root of the ring finger to measure bio-vibration signals of the finger, from which the information about heartbeat were isolated and extracted. The vibration sensor is a condenser-type 3-layer structure piezoelectric element in which a piezoelectric material 15 mmφ is placed between metal electrodes (20 mmφ). The metal plate on the skin side is protected with a round-shape rubber so that vibrations are indirectly detected through the rubber that is in contact with the skin.

Similarly, the bracelet-type bio-vibration signal measuring device was attached to the wrist of a subject to measure bio-vibration signals with the vibration sensor placed at the middle of the wrist (between the ulnar artery 113 and radial artery 114 in FIG. 17) or above the radial artery 114.

Because pressure wave caused by the ventricular contraction reaches the peripheral parts in the limbs throughout the arterial wall, the pressure pulse in the finger or wrist changes in response to each heartbeat. This pressure pulse is modulated by respiration. Measurement of the pressure pulse responses therefore allows capture of movements of the heart or breathing. The concerned pressure pulse responses are transmitted to the piezoelectric sensor as vibration waves through the surface of the finger or wrist, and then the sensor generates electromotive force on the order of μV. Because such signals contained not only intended biological information about heartbeat and breathing but also interfering noise signals, the biological information about heartbeat and breathing were isolated and extracted subsequently using the signal processing algorithm (electronic circuit and software). In addition, for simultaneous comparison, an electrode for electrocardiogram was affixed to the chest of the subject to measure the electrocardiogram (ECG) with a monopolar lead, and a hot-wire breathing flowmeter was used to obtain measured values on the breathing pattern.

Figure 19:
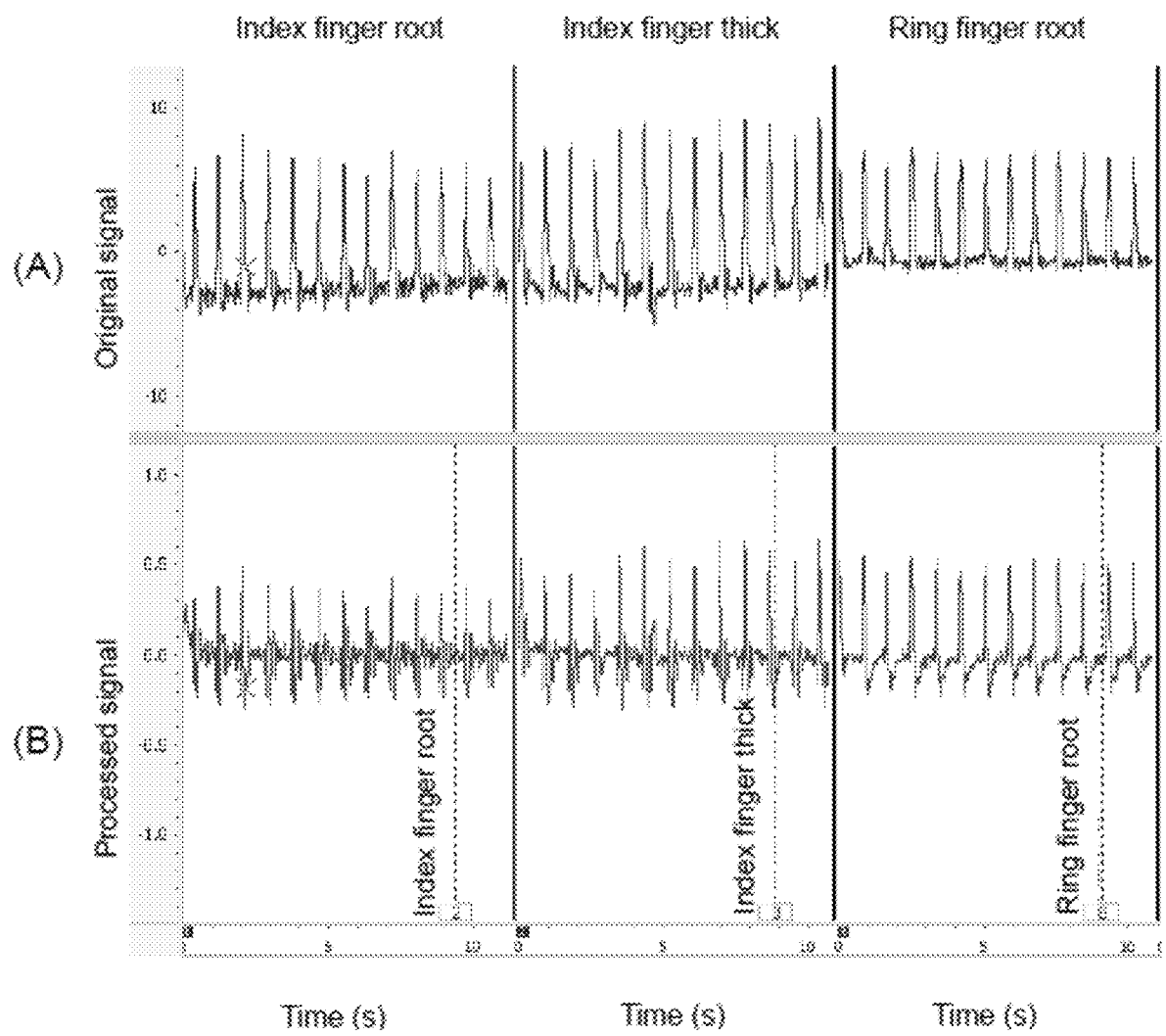
FIG. 19 (A) shows original bio-vibration signals detected through the figure of a subject; and (B) shows wave forms of the signal after processing.

FIG. 19 (A) shows original bio-vibration signals detected at the root and thick of the index finger and the root of the ring finger in order from left to right. FIG. 19 (B) shows wave forms of the subsequently processed signals (after differentiation of heartbeat-derived vibration component wave forms obtained by the full-wave rectification integration). As shown in FIG. 19 (B), the processed signals can be obtained at similar strengths irrespective of the site of the fingers of a subject.

Figure 20:
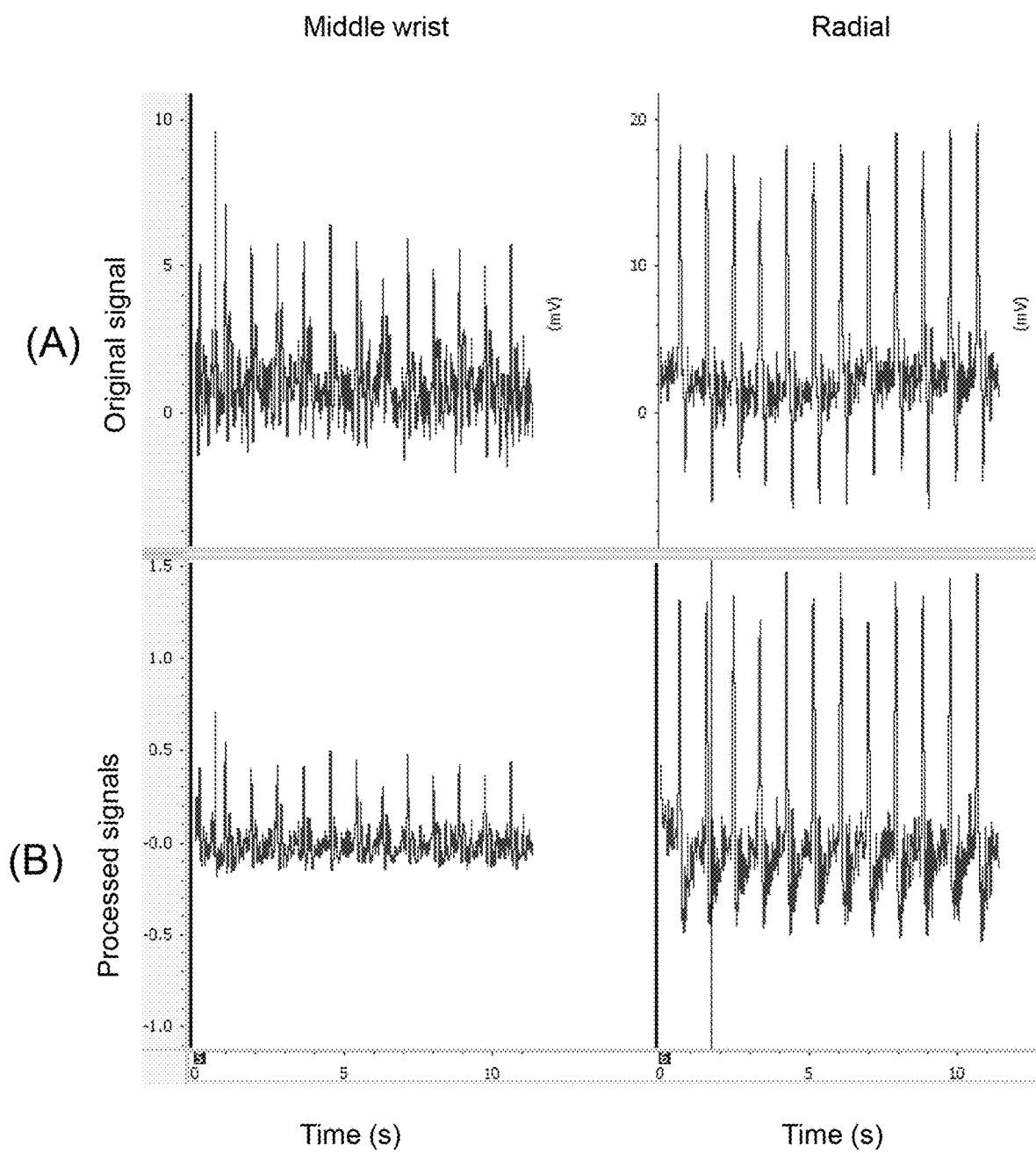
FIG. 20 (A) shows original bio-vibration signals detected through the wrist of a subject; and (B) shows wave forms of the signal after processing.

FIG. 20 (A) shows original bio-vibration signals detected at the middle of the wrist of the subject and above the radial artery on the thumb side of the wrist in order from left to right. FIG. 20 (B) shows wave forms of the subsequently processed signals (after differentiation of heartbeat-derived vibration component wave forms obtained by the full-wave rectification integration). As shown in FIG. 20 (B), the processed signals at the middle of the wrist have a smaller amplitude than those above the radial artery, indicating that the strength of available bio-vibration signals remarkably differs depending on the site of the wrist.

Figure 21:
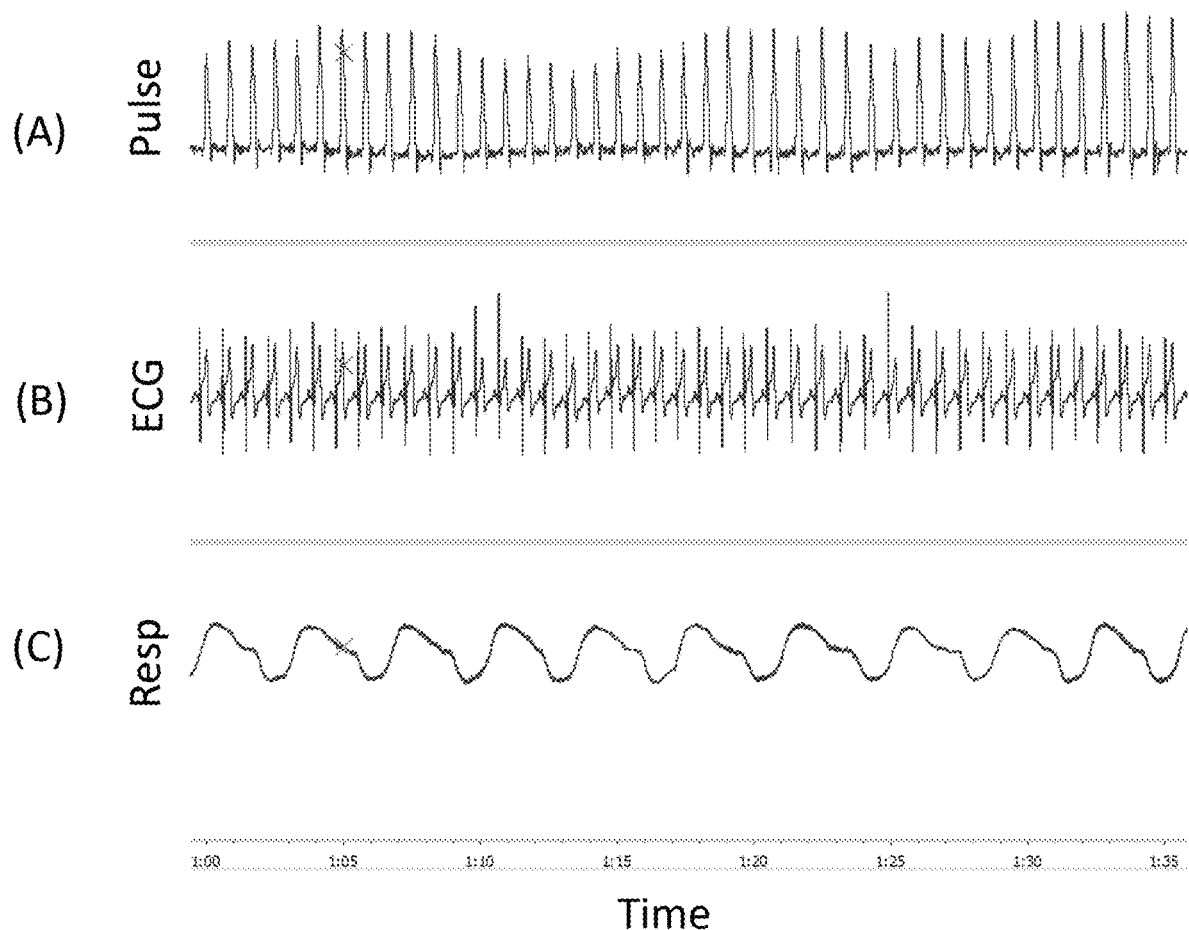
FIGS. 21 (A), (B), and (C) shows examples of heartbeat pulse obtained from bio-vibration signals, heartbeat pulse obtained from electrocardiogram, and measured breathing pattern, respectively.

FIG. 21 (A) shows an example of heartbeat pulses obtained from the bio-vibration signals (wave forms after signal processing) of the finger. FIG. 21 (B) shows heartbeat pulses obtained from the electrocardiogram measured for comparison, and FIG. 21 (C) shows breathing pattern (breathing airflow rate wave forms) measured for comparison.

Example 5

In this example, bio-vibration signals were measured at the finger of a subject at the supine, sitting, and standing positions with the ring-type bio-vibration signal measuring device attached to the root of the index finger. From the bio-vibration signals of the finger, information about heartbeat and information about breathing were isolated and extracted to calculate phase coherence. The vibration sensor was placed in indirect contact with the skin through the rubber, as explained in Example 4, to detect vibrations. In addition, for simultaneous comparison, an electrode for electrocardiogram was affixed to the chest of the subject to measure the electrocardiogram (ECG) with a monopolar lead, and a hot-wire breathing flowmeter was used to obtain measured values on the breathing pattern.

Bio-vibration signals as well as electrocardiogram and breathing flow rate wave forms at the finger and wrist were sampled at 100 Hz and saved. Bio-vibration signals were processed using specified digital filters for detection of heartbeat and breathing as follows: Bio-vibration signals were passed through high frequency band-pass filter (or high-pass filter) followed by full-wave rectification integration at a time constant of 0.1 to 0.2 seconds to extract heartbeat-derived vibration component only; for determination of peaks of the above wave forms, the extracted heartbeat-derived vibration component wave forms were differentiated; by setting the threshold, peaks (heartbeat pulse) were detected; and from intervals between the peaks, beating intervals were determined. In this section, heart rate interval determined from the electrocardiogram and one from the bio-vibration signals are referred to as RRI and BBI, respectively. In addition, bio-vibration signals were passed through low frequency band-pass filter (or low-pass filter) to extract breathing-derived vibration component, from which breathing pattern was estimated. RRI and BBI were re-sampled at 10 Hz by spline interpolation. Breathing pattern measured with the hot-wire breathing flowmeter and that estimated from the bio-vibration signals were also re-sampled at 10 Hz. Respiratory sinus arrhythmia and breathing pattern were subjected to Hilbert transformation; from the analytic signals, instantaneous phases were determined; and from their phase difference Ψ, phase coherence λ was calculated. The phase coherence was determined by shifting a 10-second calculation window by 5 seconds at a time.

Figure 22:
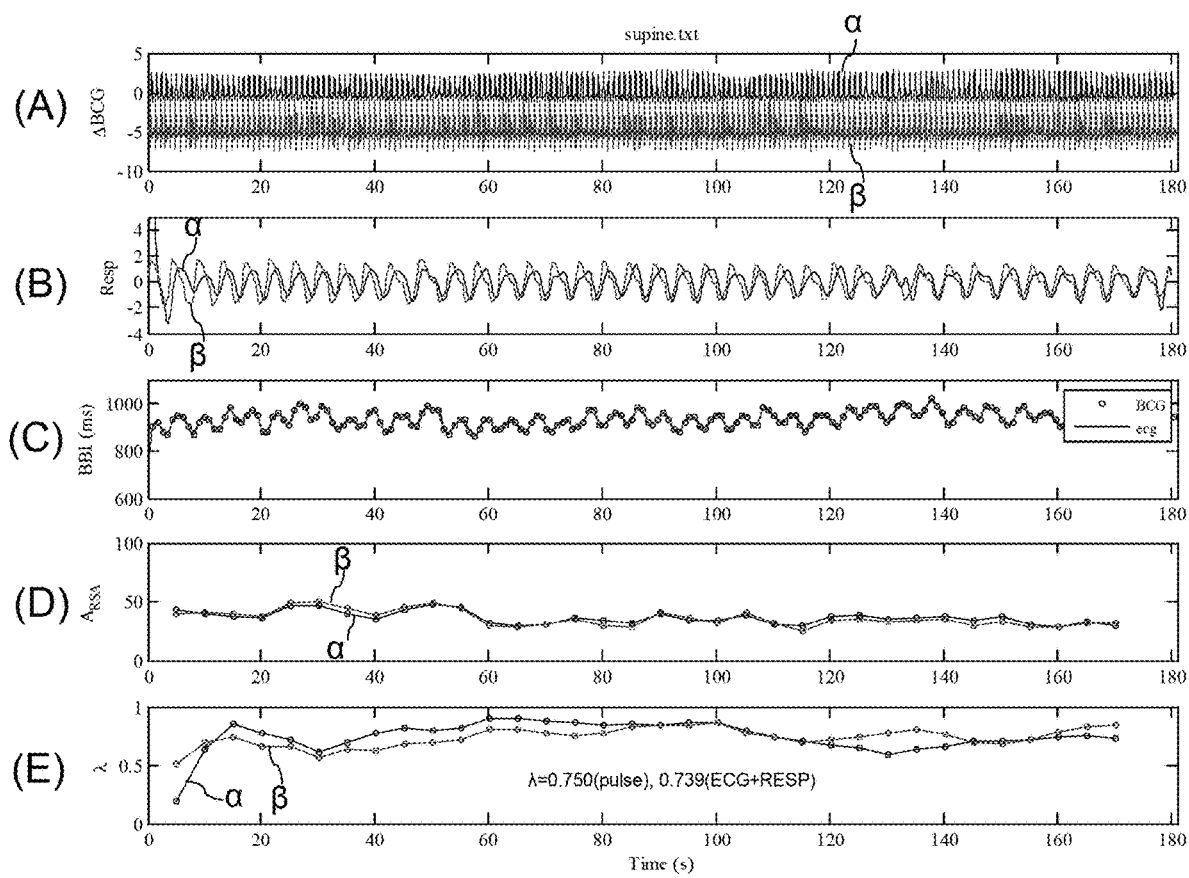
FIG. 22 The figure shows various signals calculated from bio-vibration signals detected at the root of the index finger of a subject at the supine position.

FIG. 22 compares various signals α obtained from bio-vibration signals detected at the root of the index finger of a subject at the "supine position" and various signals β obtained from the electrocardiogram or measured breathing pattern. FIG. 22 (A) shows heartbeat pulse (wave form α) obtained from the bio-vibration signals at the root of the index finger at the top and heartbeat pulse (wave form β) obtained from the electrocardiogram at the bottom. FIG. 22 (B) shows breathing pattern (wave form α) estimated from the bio-vibration signals at the root of the index finger and measured breathing pattern (wave form β). FIG. 22 (C) shows heart rate interval BBI (circle) estimated from the bio-vibration signals at the root of the index finger and heart rate interval (solid line) obtained from the electrocardiogram. FIG. 22 (D) shows amplitude (wave form α) of respiratory sinus arrhythmia estimated from the bio-vibration signals at the root of the index finger and amplitude (wave form β) of respiratory sinus arrhythmia from the electrocardiogram. FIG. 22 (E) shows phase coherence (wave form α) estimated from the bio-vibration signals at the root of the index finger and phase coherence (wave form β) calculated from the electrocardiogram and measured breathing pattern.

As shown in FIG. 22 (A), the heartbeat pulse (wave form α) obtained from the bio-vibration signals at the finger is approximate to heartbeat pulse (wave form β) obtained from the measured electrocardiogram. As shown in FIG. 22 (B), the breathing pattern (wave form α) estimated from the bio-vibration signals at the finger is approximate to the measured breathing pattern (wave form β). As shown in FIG. 22 (C), the heart rate interval BBI (circle) estimated from the bio-vibration signals at the finger is closely similar to the heart rate interval RRI (solid line) obtained from the simultaneously measured electrocardiogram, demonstrating successful calculation of fluctuations in heartbeat interval from the bio-vibration signals at the finger through signal processing. As shown in FIG. 22 (D), the amplitude of respiratory sinus arrhythmia (wave form α) estimated from the bio-vibration signals at the finger almost agrees with amplitude (wave form β) of respiratory sinus arrhythmia obtained from the electrocardiogram. Furthermore, as shown in FIG. 22 (E), the phase coherence (wave form α) calculated only from the bio-vibration signals at the finger is approximate to the phase coherence (wave form β) calculated from the electrocardiogram and measured breathing pattern. As demonstrated above, only measurement of bio-vibration signals at the finger successfully allowed calculation of fluctuations in heartbeat interval (respiratory sinus arrhythmia), breathing pattern, and phase coherence.

Figure 23:
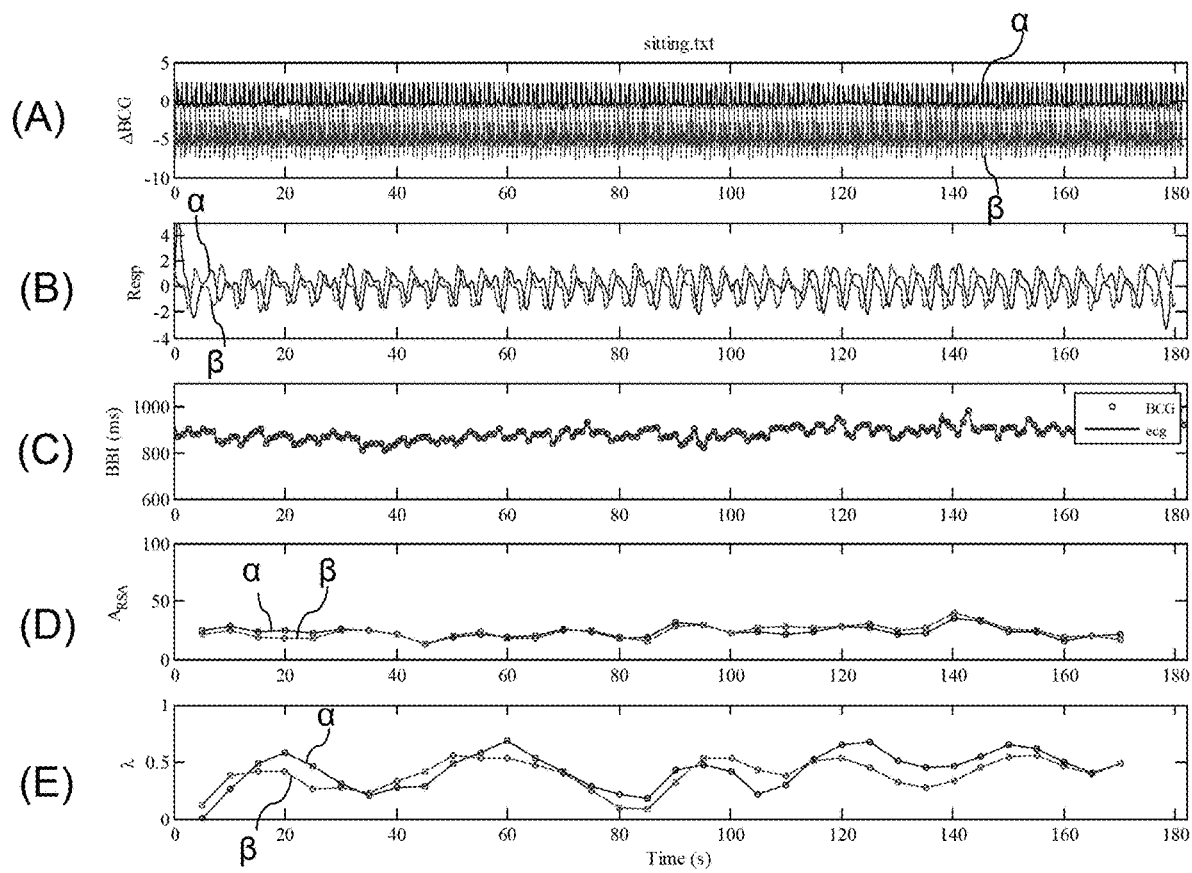
FIG. 23 The figure shows various signals calculated from bio-vibration signals detected at the root of the index finger of a subject at the sitting position.

FIG. 23 compares various signals α obtained from bio-vibration signals detected at the root of the index finger of a subject at the "sitting position" and various signals β obtained from the electrocardiogram or measured breathing pattern. Signals used in FIG. 23 (A) to FIG. 23 (E) are the same ones as used in FIG. 22 (A) to FIG. 22 (E).

As shown in FIG. 23 (A), the heartbeat pulse (wave form α) obtained from the bio-vibration signals at the finger is approximate to heartbeat pulse (wave form β) obtained from the measured electrocardiogram. As shown in FIG. 23 (B), the breathing pattern (wave form α) estimated from the bio-vibration signals at the finger is approximate to the measured breathing pattern (wave form β), although some phase shifts are observed. As shown in FIG. 23 (C), the heart rate interval BBI (circle) estimated from the bio-vibration signals at the finger is closely similar to the heart rate interval RRI (solid line) obtained from the simultaneously measured electrocardiogram. As shown in FIG. 23 (D), the amplitude of respiratory sinus arrhythmia (wave form α) estimated from the bio-vibration signals at the finger almost agrees with amplitude (wave form β) of respiratory sinus arrhythmia obtained from the electrocardiogram. Furthermore, as shown in FIG. 23 (E), the phase coherence (wave form α) calculated only from the bio-vibration signals at the finger has fluctuations similar to that of the phase coherence (wave form β) calculated from the electrocardiogram and measured breathing pattern.

Figure 24:
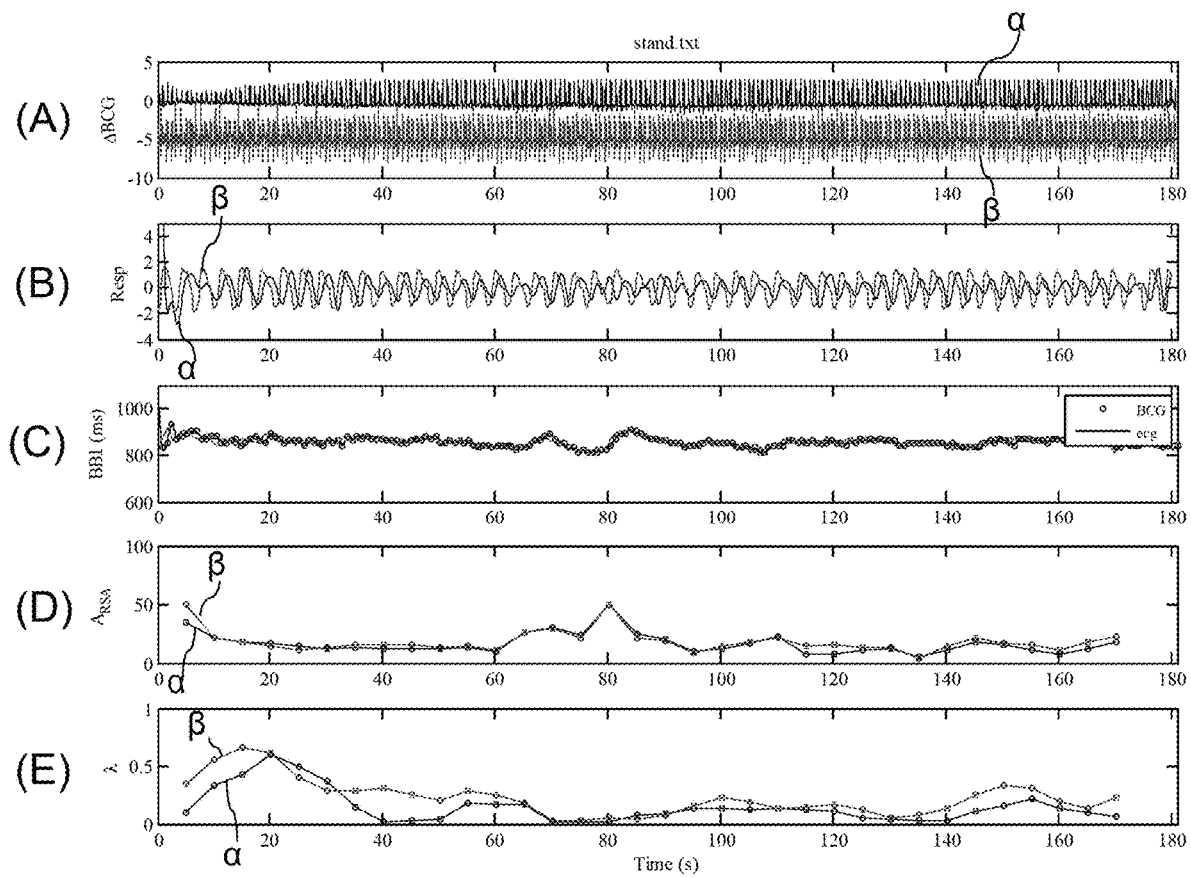
FIG. 24 The figure shows various signals calculated from bio-vibration signals detected at the root of the index finger of a subject at the standing position.

FIG. 24 compares various signals α obtained from bio-vibration signals detected at the root of the index finger of a subject at the "standing position" and various signals β obtained from the electrocardiogram or measured breathing pattern. Signals used in FIG. 24 (A) to FIG. 24 (E) are the same ones as used in FIG. 22 (A) to FIG. 22 (E).

As shown in FIG. 24 (A), the heartbeat pulse (wave form α) obtained from the bio-vibration signals at the finger is approximate to heartbeat pulse (wave form β) obtained from the measured electrocardiogram. As shown in FIG. 24 (B), the breathing pattern (wave form α) estimated from the bio-vibration signals at the finger is approximate to the measured breathing pattern (wave form β), although some phase shifts are observed. As shown in FIG. 24 (C), the heart rate interval BBI (circle) estimated from the bio-vibration signals at the finger is closely similar to the heart rate interval RRI (solid line) obtained from the simultaneously measured electrocardiogram. As shown in FIG. 24 (D), the amplitude of respiratory sinus arrhythmia (wave form α) estimated from the bio-vibration signals at the finger almost agrees with amplitude (wave form β) of respiratory sinus arrhythmia obtained from the electrocardiogram. Furthermore, as shown in FIG. 24 (E), the phase coherence (wave form α) calculated only from the bio-vibration signals at the finger has fluctuations similar to that of the phase coherence (wave form β) calculated from the electrocardiogram and measured breathing pattern.

Figure 25:
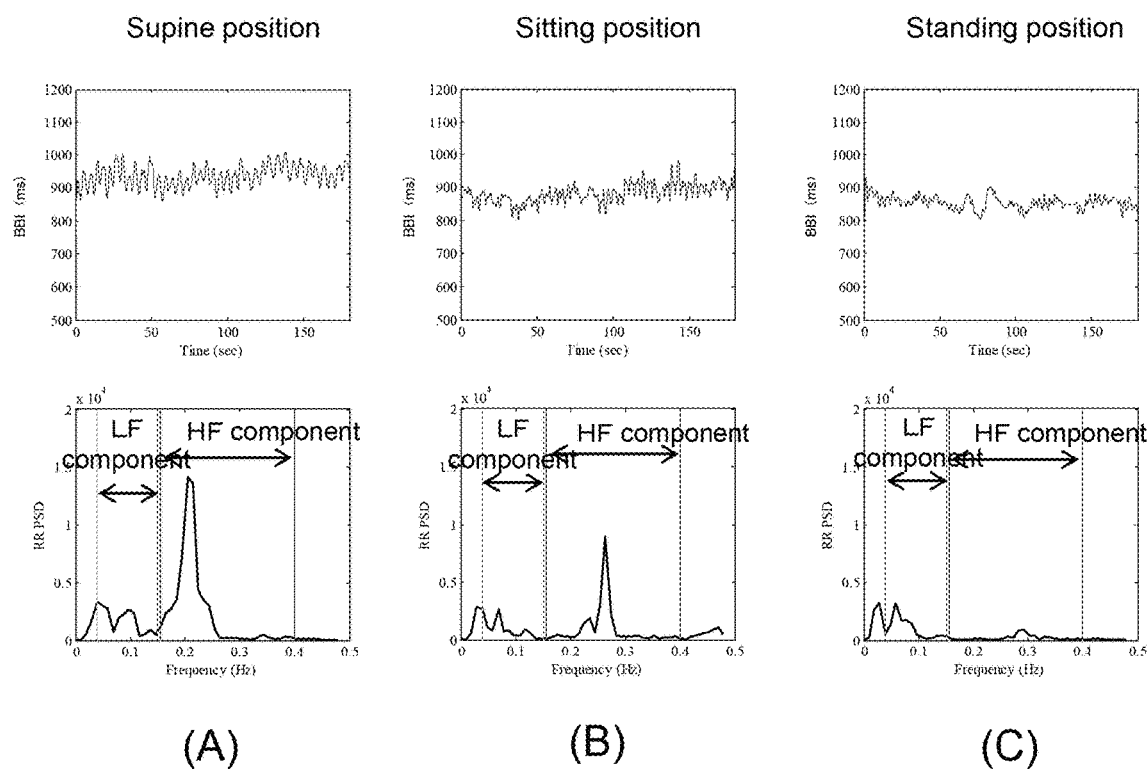
FIG. 25 (A) shows heart rate interval RRI estimated from bio-vibration signals; and (B) shows power spectral densities of RRI interval.

FIG. 25 (A) shows heart rate interval BBI (top) estimated from the bio-vibration signals (FIG. 22) detected at the root of the index finger of a subject at the "supine position" and the power spectrum wave forms thereof (bottom). FIG. 25 (B) shows heart rate interval BBI (top) estimated from the bio-vibration signals (FIG. 23) detected at the root of the index finger of a subject at the "sitting position" and its power spectral density (bottom). FIG. 25 (C) shows heart rate interval BBI (top) estimated from the bio-vibration signals (FIG. 24) detected at the root of the index finger of a subject at the "standing position" and its power spectral density (bottom). As shown in the bottom charts in FIG. 25 (A) to FIG. 25 (C), the high frequency component (HF component) is the largest when measured at the supine position followed by the sitting position and standing position in this order.

Figure 26:
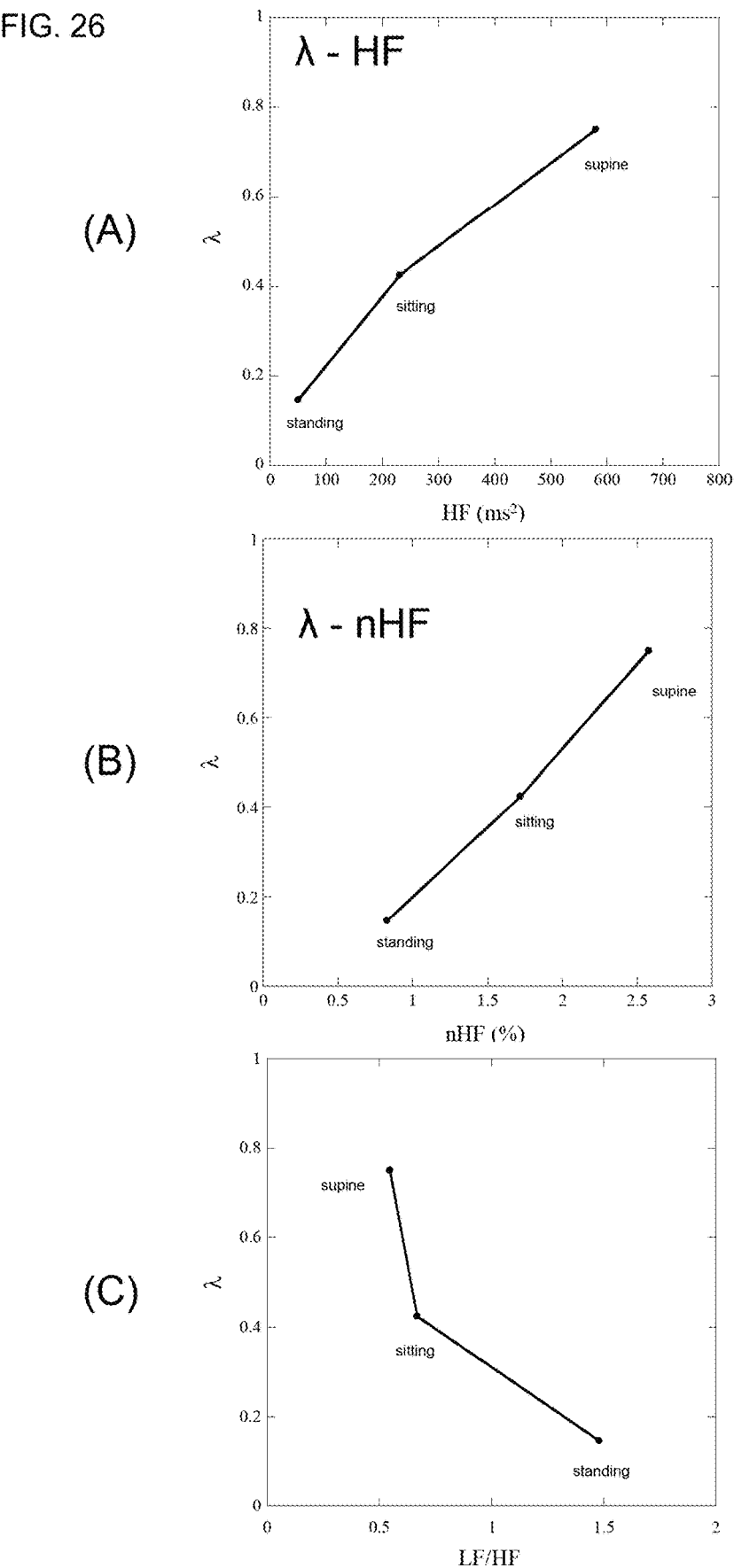
FIG. 26 The figure shows a relationship of phase coherence λ obtained from bio-vibration signals with power spectrum component of the heart rate interval.

FIG. 26 shows relationships between phase coherence λ and power spectrum of heart rate interval determined from bio-vibration signals detected at the root of the index finger of a subject at the supine position, sitting position, or standing position. FIG. 26 (A) shows a relationship between the phase coherence λ at the supine position, sitting position, or standing position and HF component power ($ms^2$) in the power spectral density in bottom charts in FIG. 25. The HF component is determined by integration of signals at frequency of 0.15 to 0.4 Hz. FIG. 26 (B) shows a relationship between the phase coherence λ at the supine position, sitting position, or standing position and power (%) of normalized HF component (nHF). The nHF value is determined by dividing the square root of the power of HF by mean BBI. FIG. 26 (C) shows a relationship between the phase coherence λ at the supine position, sitting position, or standing position and the ratio of power of low frequency component (LF component) to that of high frequency component (HF component) (LF/HF power ratio).

In general, the HF component is affected by parasympathetic neural activity associated with breathing, while the LF component is affected by sympathetic and parasympathetic neural activities. The power of the HF component at each position represents the parasympathetic neural function, while the LF/HF power ratio represents the sympathetic neural function.

As shown in FIG. 26 (A) and FIG. 26 (B), the phase coherence λ is positively correlated with the power of the HF component. As shown in FIG. 26 (C), on the other hand, the phase coherence λ is negatively correlated with the LF/HF power ratio. The HF and nHF are said to reflect the cardiac parasympathetic neural activity. In addition, the LF/HF power ratio is said to reflect the sympathetic neural activity. The phase coherence λ, accordingly, represents balance of the cardiac autonomic activity; the phase coherence λ of zero (0) indicates a sympathetic dominant state, while one (1) indicates a parasympathetic dominant state, indirectly. As shown in FIG. 26, at the supine position, phase coherence λ as well as HF component and nHF component are large, leading to small LF/HF power ratio; at the sitting position, these values are smaller than those at the supine position, leading to large LF/HF power ratio; and at the standing position, these values are further decreased, leading to further increased LF/HF power ratio. As described above, biological information obtained from the bio-vibration signals at the finger can be used as an indicator of the autonomic nervous activity.

Example 6

In this example, a bracelet-type bio-vibration signal measuring device was applied to the upper arm (between the elbow and shoulder) of a subject at the sitting position. The sensor was configured as follows: the both whole surfaces of a PVDF thin-film 40 μm in thickness were coated with carbon electrode 1 μm in thickness; the both coated surfaces were further laminated with a PET film 25 μm in thickness to protect the PVDF film; and the protected surfaces were further covered with an aluminum thin film (aluminum foil/PET-layered film) for electromagnetic shielding so that the sensor finally had a size of 8 cm in width, 12 cm in length, and 0.5 mm in thickness. The concerned sheet sensor was wrapped around a semicircumference of the upper arm to measure bio-vibration signals (pulse waves) at the upper arm, from which information about heartbeat and information about breathing were isolated and extracted to calculate the phase coherence. The vibration sensor was implemented on the inside of a band, which was wrapped around the upper arm. The vibration sensor detected vibrations in indirect contact with the skin through a thin organic film sheet several microns in thickness. In addition, for simultaneous comparison, an electrode for electrocardiogram was affixed to the chest of the subject to measure the electrocardiogram (ECG) with a monopolar lead.

Figure 27:
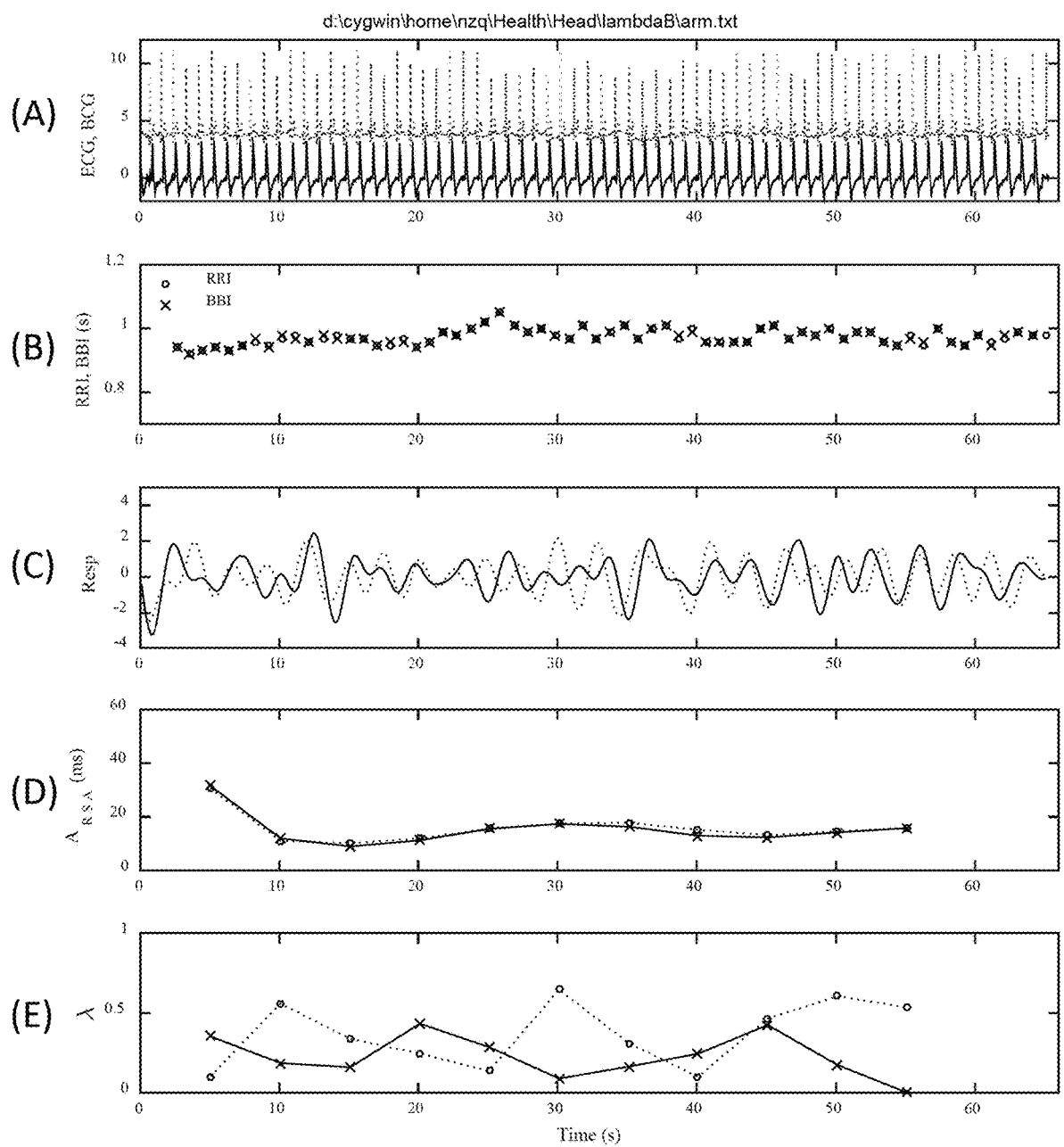
FIG. 27 The figure shows various signals calculated from bio-vibration signals detected at the upper arm of a subject at the sitting position.

FIG. 27 compares various signals (solid line, cross) obtained from bio-vibration signals detected at the upper arm and various signals (dotted line, circle) obtained from the electrocardiogram. FIG. 27 (A) shows heartbeat pulse (solid line) obtained from the bio-vibration signals at the upper arm and heartbeat pulse (dotted line) obtained from the electrocardiogram. FIG. 27 (B) shows heart rate interval BBI (cross) estimated from peaks in the bio-vibration signals at the upper arm and heart rate interval (circle) obtained from peaks in the electrocardiogram. FIG. 27 (C) shows breathing pattern (solid line) estimated from fluctuations in peak interval in the bio-vibration signals at the upper arm and breathing pattern (dotted line) estimated from fluctuations in peak interval (heart rate interval) in the electrocardiogram. FIG. 27 (D) shows amplitude (solid line) of respiratory sinus arrhythmia estimated from the bio-vibration signals at the upper arm and amplitude (dotted line) of respiratory sinus arrhythmia obtained from the electrocardiogram. FIG. 27 (E) shows phase coherence (solid line) estimated from the bio-vibration signals at the upper arm and phase coherence (dotted line) calculated from the electrocardiogram.

As shown in FIG. 27 (A), the heartbeat pulse (solid line) obtained from the bio-vibration signals at the upper arm is approximate to heartbeat pulse (dotted line) obtained from the measured electrocardiogram. As shown in FIG. 27 (B), the heart rate interval BBI (cross) estimated from the bio-vibration signals at the upper arm is closely similar to the heart rate interval RRI (circle) obtained from the simultaneously measured electrocardiogram, demonstrating successful calculation of fluctuations in heartbeat interval from the bio-vibration signals at the upper arm through signal processing. In addition, as shown in FIG. 27 (C), breathing pattern (solid line) estimated from the bio-vibration signals at the upper arm and breathing pattern (dotted line) estimated from the electrocardiogram slightly differ in wave forms, and thus calculation of the breathing pattern using the same algorithm was not appropriate in this example. As shown in FIG. 27 (D), the amplitude of respiratory sinus arrhythmia (solid line) estimated from the bio-vibration signals at the upper arm almost agrees with amplitude (dotted line) of respiratory sinus arrhythmia obtained from the electrocardiogram. Furthermore, as shown in FIG. 27 (E), between the phase coherence (solid line) calculated only from the bio-vibration signals at the upper arm and phase coherence (dotted line) calculated from the electrocardiogram, a correlation is partially observed although substantial shifts are also partially observed. A trend in phase coherence can be identified from the bio-vibration signals at the upper arm. As demonstrated above, only measurement of bio-vibration signals at the upper arm successfully allowed calculation of fluctuations in heartbeat interval (respiratory sinus arrhythmia), breathing pattern, and phase coherence.

Example 7

In this example, a rectangle thin sensor (5 cm in width, 5 cm in length) was fabricated as done in Example 6 and integrated into a rubber band part of a head-band-type bio-vibration signal measuring device. The device was attached to the head of a subject at the sitting position to measure bio-vibration signals at the temple, from which information about heartbeat and information about breathing were isolated and extracted to calculate phase coherence. The vibration sensor implemented on the head band was attached to the head by wrapping the band. The vibration sensor detected vibrations in indirect contact with the temple skin through the rubber. In addition, for simultaneous comparison, an electrode for electrocardiogram was affixed to the chest of the subject to measure the electrocardiogram (ECG) with a monopolar lead.

Figure 28:
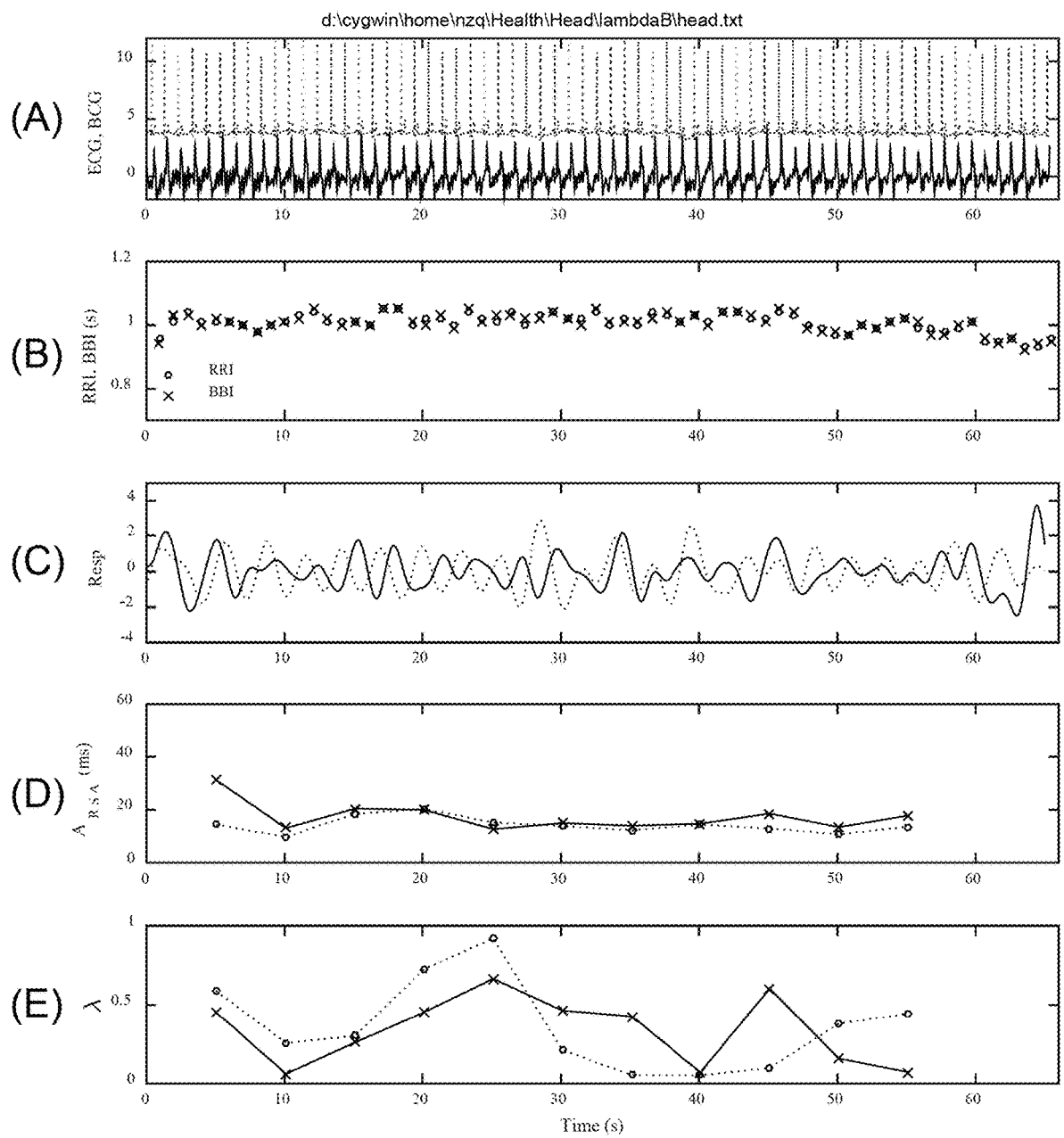
FIG. 28 The figure shows various signals calculated from bio-vibration signals detected at the temple of a subject at the standing position.

FIG. 28 compares various signals (solid line, cross) obtained from bio-vibration signals detected at the temple and various signals (dotted line, circle) obtained from the electrocardiogram. FIG. 28 (A) shows heartbeat pulse (solid line) obtained from the bio-vibration signals at the temple and heartbeat pulse (dotted line) obtained from the electrocardiogram. FIG. 28 (B) shows heart rate interval BBI (cross) estimated from peaks in the bio-vibration signals at the temple and heart rate interval (circle) obtained from peaks in the electrocardiogram. FIG. 28 (C) shows breathing pattern (solid line) estimated from fluctuations in peak interval in the bio-vibration signals at the temple and breathing pattern (dotted line) estimated from fluctuations in peak interval in the electrocardiogram. FIG. 28 (D) shows amplitude (solid line) of respiratory sinus arrhythmia estimated from the bio-vibration signals at the temple and amplitude (dotted line) of respiratory sinus arrhythmia obtained from the electrocardiogram. FIG. 28 (E) shows phase coherence (solid line) estimated from the bio-vibration signals at the temple and phase coherence (dotted line) calculated from the electrocardiogram.

As shown in FIG. 28 (A), the heartbeat pulse (solid line) obtained from the bio-vibration signals at the temple is approximate to heartbeat pulse (dotted line) obtained from the measured electrocardiogram. As shown in FIG. 28 (B), the heart rate interval BBI (cross) estimated from the bio-vibration signals at the temple is closely similar to the heart rate interval RRI (circle) obtained from the simultaneously measured electrocardiogram, demonstrating successful calculation of fluctuations in heartbeat interval from the bio-vibration signals at the temple through signal processing. In addition, as shown in FIG. 28 (C), breathing pattern (solid line) estimated from the bio-vibration signals at the temple and breathing pattern (dotted line) estimated from the electrocardiogram slightly differ in wave forms, and thus calculation of the breathing pattern using the same algorithm was not appropriate in this example. As shown in FIG. 28 (D), the amplitude of respiratory sinus arrhythmia (solid line) estimated from the bio-vibration signals at the temple almost agrees with amplitude (dotted line) of respiratory sinus arrhythmia obtained from the electrocardiogram. Furthermore, as shown in FIG. 28 (E), between the phase coherence (solid line) calculated only from the bio-vibration signals at the temple and phase coherence (dotted line) calculated from the electrocardiogram, a correlation is partially observed although shifts are also partially observed. A trend in phase coherence can be identified from the bio-vibration signals at the temple. As demonstrated above, only measurement of bio-vibration signals at the temple successfully allowed calculation of fluctuations in heartbeat interval (respiratory sinus arrhythmia), breathing pattern, and phase coherence.

One modality of the ring-type, bracelet-type, or band-type bio-vibration signal measuring device in this invention can measure sleep state using the finding that amplitude of δ wave is correlated with phase coherence of instantaneous phase difference between fluctuations in heartbeat interval and breathing pattern. Because the phase coherence is insusceptible to breathing frequency, sleep state can be measured at improved accuracy. In addition, one modality of the ring-type, bracelet-type, or band-type bio-vibration signal measuring device in this invention can be served as a less-burdensome, less-stressful, and handy sleep state measuring device. The phase coherence can be measured in real time, allowing measurement of onset time point of non-REM sleep time and rhythm cycle of non-REM to REM sleep, and thereby the sleep state can be identified accurately. In addition, the device measures or extracts breathing pattern at the same time so that apneic state during sleep can be also detected. Furthermore, size of respiratory sinus arrhythmia in a subject can be measured as an auxiliary assessment indicator of sleep state.

Furthermore, the sleep state measuring device provided with one modality of the ring-type, bracelet-type, or band-type bio-vibration signal measuring device in this invention, if any, may have a function to assess sleep state based on the calculated phase coherence. In the assessment function, for example, if the calculated phase coherence is larger than the threshold, the sleep state may be assessed as a deep state; or if it is smaller than the threshold, the sleep state may be assessed as a shallow state; the sleep quality may be evaluated based on the duration in which the phase coherence remains higher than the threshold; or the sleep quality may be evaluated based on the cycle of fluctuations of the phase coherence. The threshold may be a predetermined value, be specified based on previously calculated phase coherence values in the measurement subject, or be set at multiple levels for step-wise evaluation of the sleep quality. Furthermore, the information processing means included in the bio-vibration signal measuring device may have a function to assess breathing state during sleep. For example, depending on the breathing pattern acquisition method, but with any acquisition method, for central sleep apnea (apnea resulted from discontinuation of breathing movement due to abnormality in the respiratory center in the brain), non-breathing state can be found based on a failure of detection of the breathing pattern due to discontinuation of the breathing movement. Furthermore, if the breathing pattern is acquired through measurement of the air flow caused by breathing, discontinuation of breathing-related air flow results in a failure of detection of the breathing pattern, and thus not only central sleep apnea but also obstructive sleep apnea (apnea caused by airway obstruction, but with breathing movement) can be found. The display output means of the bio-vibration signal measuring device may output results such as sleep state presented with the assessment function.

Furthermore, the bio-vibration signal measuring device provided with the phase coherence calculation function in this invention may be served as a stress state measuring device, because phase coherence can be used in evaluation of not only sleep state but also mental stress.

The bio-vibration signal measuring device in this invention can be integrated in various ornaments and electronic devices. For example, a sensor for measurement of vibrations may be integrated in a bracelet, watch, or ring to measure stress state of the user. In addition, bio-vibration signals acquired with the bio-vibration signal measuring device or subsequently obtained biological information can be transmitted through communication means to portable terminals or computers in which the phase coherence calculation device is integrated so that mental stress can be evaluated in various situations of daily life. Furthermore, state of an operator in a car, train, or air plane can be controlled by communication of the biological information. The bio-vibration signal measuring device in this invention can be wrapped or affixed around a column component or a part of the body of a subject to acquire bio-signals such as pulse wave. In this device, communication and battery functions such as Bluetooth (trademark) and Zigbee (trademark) can be integrated. If this device is affixed to workers at a tunnel or underground construction site to acquire bio-vibration signals such as pulse wave during their work in real time, it can be used for health management of the workers. In addition, if this device is integrated in brassiere for females to acquire bio-signals such as heartbeat and breathing, it can be used for health management of females. If the sensor is inserted in a maternity girdle, this device can be used for health management of pregnant women or to acquire fetal biological information such as vibration signals of heartbeat and movement.

The bio-vibration signal measuring device in this invention can be applied to acquisition of biological information from not only humans but also experimental animals such as guinea pigs, companion animals such as dogs, cats, rabbits, and hamsters, and livestock such as cattle, horses, and sheep. The device can be attached to a body part of the above subjects, using collar, bracelet, bangle, and ear ring.

LEGEND

1 Sleep state measuring device
2 Information acquisition part
3 Information processing part
4 Operation part
5 Output part
6 Memory part

What is claimed:

1. A sleep state measuring device comprising:
a phase coherence calculation means for calculating phase coherence ($\lambda$) based on an instantaneous phase difference ($\psi$) between an instantaneous phase of fluctuations in heartbeat interval ($\psi$h) obtained during a time series (t) of a subject's sleep and an instantaneous phase in breathing pattern ($\psi$r) of the subject during said time series (t), wherein:

$$\psi(t)=\psi h(t)-\psi r(t)+2n\pi$$

where n is an integer such that $-\pi \leq \psi \leq \pi$;
and wherein the phase coherence $\lambda$ at time $t_k$ is calculated according to Equation (1) below:

$$\lambda(t_k) = \left| \frac{1}{N} \sum_{j=k-N/2}^{k+N/2} e^{i\Psi(t_j)} \right|; \quad (1)$$

where N is a number of consecutive data samples; and
an information processing means for assessing a sleep state of the subject based on the phase coherence, identifying an onset time point of non-REM sleep, and measuring a rhythm cycle of the non-REM to REM sleep.

2. The sleep state measuring device of claim 1, further comprising an electrocardiogram measuring sensor and a breathing wave form extraction means for extracting signals related to breathing pattern from an electrocardiogram of the subject measured with said electrocardiogram measuring sensor.

3. The sleep state measuring device of claim 2, wherein sampling frequency of said electrocardiogram measuring sensor is not less than 100 Hz.

4. The sleep state measuring device of claim 2, wherein said electrocardiogram measuring sensor is a wearable sensor attachable to the subject.

5. The sleep state measuring device of claim 4, wherein said wearable sensor is attachable to a limb or the head of the subject.

6. The sleep state measuring device of claim 1, further comprising a vibration measuring sensor, a heart rate interval calculation means for calculating the fluctuations in heartbeat interval from signals measured with said vibration measuring sensor, and a breathing wave form extraction means for extracting signals related to the breathing pattern from signals measured with said vibration measuring sensor.

7. The sleep state measuring device of claim 1, wherein said information processing means further assesses a breathing state of the subject based on said breathing pattern.

8. A method of measuring sleep state of a subject, comprising:
acquiring heartbeat information and breathing information obtained during a time series (t) of the subject's sleep; and
calculating phase coherence ($\lambda$) based on an instantaneous phase difference ($\psi$) between an instantaneous phase of fluctuations in heartbeat interval ($\psi$h) and an instantaneous phase in breathing pattern ($\psi$r) based on said acquired heartbeat information and said breathing information obtained during said time series (t), wherein:

$$\psi(t)=\psi h(t)-\psi r(t)+2n\pi$$

where n is an integer such that $-\pi \leq \psi \leq \pi$;
and wherein the phase coherence $\lambda$ at time $t_k$ is calculated according to Equation (1) below:

$$\lambda(t_k) = \left| \frac{1}{N} \sum_{j=k-N/2}^{k+N/2} e^{i\Psi(t_j)} \right|; \quad (1)$$

wherein N is a number of consecutive data samples; and
assessing the sleep state of the subject based on the calculated phase coherence.

9. The method of claim 8, wherein said heartbeat information is measured via electrocardiogram, and signals related to the breathing pattern are obtained from the measured electrocardiogram.

10. The method of claim 8, wherein said heartbeat information is measured via ballistocardiogram or bio-vibration signals, and signals related to the fluctuations in heartbeat interval and breathing frequency are obtained from the measured ballistocardiogram or the bio-vibration signals.

11. The method of claim 10, further comprising estimating a transfer characteristic of ballistocardioaction from the measured ballistocardiogram or the bio-vibration signals of the subject, and applying an inverse transfer function of said transfer characteristic to the measured ballistocardiogram or the bio-vibration signals of the subject, thereby obtaining heartbeat wave forms.

12. A sleep state measuring device, comprising:
acquisition means for acquiring biological information comprising heartbeat information and breathing information of a subject during a time series (t);
a breathing wave form extraction means for extracting breathing pattern from said biological information;
a heart rate interval calculation means for calculating fluctuations in heartbeat interval from said biological information; and
a phase coherence calculation means for calculating phase coherence ($\lambda$) based on an instantaneous phase difference ($\psi$) between an instantaneous phase in said breathing pattern ($\psi$r) and an instantaneous phase in said fluctuations in heartbeat interval ($\psi$h) during said time series (t), wherein:

$$\psi(t)=\psi h(t)-\psi r(t)+2n\pi$$

where n is an integer such that $-\pi \leq \psi \leq \pi$;

and wherein the phase coherence λ at time $t_k$ is calculated according to Equation (1) below:

$$\lambda(t_k) = \left| \frac{1}{N} \sum_{j=k-N/2}^{k+N/2} e^{i\Psi(t_j)} \right|; \quad (1)$$

wherein N is a number of consecutive data samples; and
an information processing means for assessing a sleep state of the subject based on the phase coherence, identifying an onset time point of non-REM sleep, and measuring a rhythm cycle of the non-REM to REM sleep.

13. The phase sleep state measuring device of claim 12, wherein said biological information comprises electrocardiograms.

14. The sleep state measuring device of claim 12, wherein said biological information comprises ballistocardiograms or bio-vibration signals.

15. The sleep state measuring device of claim 12, wherein said biological information are acquired at a sampling frequency of not less than 100 Hz.

16. The sleep state measuring device of claim 12, wherein said acquisition means comprises a wearable sensor attachable to the subject.

17. The sleep state measuring device of claim 16, wherein said wearable sensor is attachable to a limb or the head of the subject.

* * * * *